US007282496B2

(12) United States Patent
Sandanayaka et al.

(10) Patent No.: US 7,282,496 B2
(45) Date of Patent: Oct. 16, 2007

(54) ALLENIC ARYL SULFONAMIDE HYDROXAMIC ACIDS AS MATRIX METALLOPROTEINASE AND TACE INHIBITORS

(75) Inventors: Vincent Premaratna Sandanayaka, Northboro, MA (US); Efren Guillermo Delos Santos, Nanuet, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 623 days.

(21) Appl. No.: 10/285,940

(22) Filed: Nov. 1, 2002

(65) Prior Publication Data

US 2003/0130238 A1 Jul. 10, 2003

Related U.S. Application Data

(60) Provisional application No. 60/336,050, filed on Nov. 1, 2001.

(51) Int. Cl.
A61P 1/00 (2006.01)
A61K 31/54 (2006.01)
A61K 31/19 (2006.01)
C07D 243/14 (2006.01)
C07D 279/00 (2006.01)

(52) U.S. Cl. ............... 514/221; 514/227.5; 514/575; 540/570; 544/58.4; 562/623

(58) Field of Classification Search ............. 514/221, 514/227.5, 575; 540/570; 544/58.4; 562/623
See application file for complete search history.

(56) References Cited

U.S. PATENT DOCUMENTS

| 5,455,258 | A | 10/1995 | MacPherson et al. | 514/357 |
|---|---|---|---|---|
| 5,506,242 | A | 4/1996 | MacPherson et al. | 514/336 |
| 5,552,419 | A | 9/1996 | MacPherson et al. | 514/357 |
| 5,753,653 | A | 5/1998 | Bender et al. | 514/227.5 |
| 5,770,624 | A | 6/1998 | Parker | 514/575 |
| 5,804,593 | A | 9/1998 | Warpehoski et al. | 514/419 |
| 5,817,822 | A | 10/1998 | Nantermet et al. | 546/194 |
| 5,929,097 | A | 7/1999 | Levin et al. | 514/351 |
| 5,962,481 | A | 10/1999 | Levin et al. | 514/352 |
| 5,977,408 | A | 11/1999 | Levin et al. | 562/622 |
| 6,162,814 | A | 12/2000 | Levin et al. | 514/336 |
| 6,162,821 | A | 12/2000 | Levin et al. | 514/407 |
| 6,172,057 | B1 | 1/2001 | Venkatesan et al. | 514/312.01 |
| 6,197,791 | B1 | 3/2001 | Venkatesan et al. | 514/327 |
| 6,197,795 | B1 | 3/2001 | Levin et al. | 514/352 |
| 6,200,996 | B1 | 3/2001 | Levin et al. | 514/347 |
| 6,225,311 | B1 | 5/2001 | Levin et al. | 514/227.5 |
| 6,277,885 | B1 | 8/2001 | Levin et al. | 514/575 |
| 6,288,086 | B1 | 9/2001 | Venkatesan | 514/327 |
| 6,326,516 | B1 | 12/2001 | Levin et al. | 562/622 |
| 6,331,563 | B1 | 12/2001 | Venkatesan et al. | 514/459 |
| 6,340,691 | B1 | 1/2002 | Levin et al. | 514/307 |
| 6,342,508 | B1 | 1/2002 | Venkatesan et al. | 514/311 |
| 6,358,980 | B1 | 3/2002 | Levin et al. | 514/330 |
| 6,441,023 | B1 | 8/2002 | Venkatesan et al. | 514/432 |
| 6,444,704 | B1 | 9/2002 | Venkatesan et al. | 514/575 |
| 6,462,073 | B2 | 10/2002 | Venkatesan et al. | 514/423 |
| 6,498,167 | B2 | 12/2002 | Levin et al. | 514/310 |
| 6,534,491 | B2 | 3/2003 | Levin et al. | 514/183 |
| 6,548,524 | B2 | 4/2003 | Levin et al. | 514/359 |
| 6,716,833 | B2 | 4/2004 | Levin et al. | 514/183 |
| 6,753,337 | B2 | 6/2004 | Levin et al. | 514/330 |
| 6,762,178 | B2 | 7/2004 | Levin et al. | 514/213.01 |

FOREIGN PATENT DOCUMENTS

| DE | 195 42 189 A1 | 5/1997 |
|---|---|---|
| EP | 606046 A1 | 7/1994 |
| EP | 757037 A2 | 2/1997 |
| EP | 757984 A1 | 2/1997 |
| EP | 803505 A1 | 10/1997 |
| WO | WO95/35275 | 12/1995 |
| WO | WO95/35276 | 12/1995 |
| WO | WO96/00214 | 1/1996 |
| WO | WO96/27583 | 9/1996 |
| WO | WO96/33172 | 10/1996 |
| WO | WO97/18194 | 5/1997 |
| WO | WO97/19068 | 5/1997 |

(Continued)

OTHER PUBLICATIONS

Borkakoti, Matrix Metalloproteases: Variations on a Theme, Progress in Biophysics & Molecular Biology, 1998, vol. 70, No. 1, pp. 73-94.*

(Continued)

*Primary Examiner*—Brenda Coleman
(74) *Attorney, Agent, or Firm*—Pepper Hamilton LLP

(57) ABSTRACT

Compounds of the formula

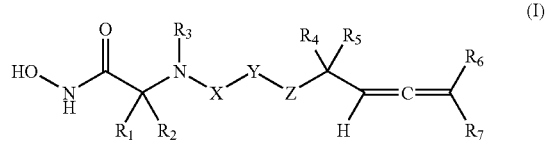

(I)

are useful in treating disease conditions mediated by TNF-α, such as rheumatoid arthritis, osteoarthritis, sepsis, AIDS, ulcerative colitis, multiple sclerosis, Crohn's disease, degenerative cartilage loss, graft rejection, cachexia, inflammation, fever, insulin resistance, septic shock, congestive heart failure, inflammatory disease of the central nervous system, inflammatory bowel disease and HIV.

15 Claims, No Drawings

FOREIGN PATENT DOCUMENTS

| | | |
|---|---|---|
| WO | WO97/20824 | 6/1997 |
| WO | WO97/22587 | 6/1997 |
| WO | WO97/27174 | 7/1997 |
| WO | 97/45402 | 12/1997 |
| WO | WO98/03166 | 1/1998 |
| WO | WO98/07697 | 2/1998 |
| WO | WO98/08815 | 3/1998 |
| WO | WO98/08822 | 3/1998 |
| WO | WO98/08823 | 3/1998 |
| WO | WO98/08825 | 3/1998 |
| WO | WO98/08827 | 3/1998 |
| WO | WO98/08853 | 3/1998 |
| WO | WO98/16503 | 4/1998 |
| WO | WO98/16506 | 4/1998 |
| WO | WO98/16514 | 4/1998 |
| WO | WO98/16520 | 4/1998 |
| WO | WO98/27069 | 6/1998 |
| WO | WO98/31664 | 7/1998 |
| WO | WO98/33768 | 8/1998 |
| WO | WO98/34918 | 8/1998 |
| WO | WO98/39313 | 9/1998 |
| WO | WO98/39329 | 9/1998 |
| WO | WO98/42659 | 10/1998 |
| WO | WO98/43963 | 10/1998 |
| WO | WO 00/44730 | 8/2000 |

OTHER PUBLICATIONS

Yu et al., Matrix Metalloproteases: Novel Targets for Directed Cancer Therapy, Drugs & Aging, Sep. 1997, vol. 11, No. 3, pp. 229-244.*
International Search Report PCT/US02/34904 Mailed Mar. 04, 2003.
Black, D. K.; Landor, S. R.; Patel, A. N.; Whiter, P. F. *J. Chem. Soc.* (C) 1967, 2260-2262.
Campbell, R. W.; Hill, H. W. *J. Org. Chem.* 1973, 38, 1047-1049.
Cowie, J. S.; Landor, P. D.; Landor, S. R. H *J. Chem. Soc.* Perkin I 1973, 720-724.
Galantay, E.; Bacso, I.; Coombs, R. V. *Synthesis* 1974, 344-346.
Keck, G. E.; Webb, R. R. *Tetrahedron Lett.* 1982, 23, 3051-3054.
Asher, Vikram; Becu, Christian; Anteunis, Marc. J. O.; Callens, Roland *Tetrahedron Lett.* 1981, 22(2), 141-144.
Old, L. *Science*, 1985, 230, 630-632.
Lathbury, D.; Gallagher, T. *J. Chem. Soc.* Chem. Comm. 1986, 114-115.
Piguet, P.F.Grau, G. E.; et al. *J. Exp. Med.* 1987, 166 1280-1289.
Kogami, Yuji; Okawa, Kenji, *Bull. Chem. Soc. Jpn.* 1987, 60(8), 2963-2965.
Mathison, et al. *J. Clin. Invest.* 1988, 81, 1925-1937.
Beutler, B.; Cerami, A. *Ann. Rev. Biochem.* 1988, 57, 505-518.
Auvin, S.; Cochet, O.; Kucharczyk, N.; Le Goffic, F.; Badet, B. *Bioorganic Chemistry*, 1991, 19, 143-151.
T. W. Greene, P. G. M. Wuts "Protective Groups in Organic Synthesis", 2nd Edition, 1991, Wiley & Sons, New York.
Miethke, et al. *J. Exp. Med.* 1992, 175, 91-98.
Peterson, P. K.; Gekker, G. et al. *J. Clin. Invest.* 1992, 89, 574-580.
Angle, S. R.; Breitenbucher, J. G.; Arnaiz, D. *O. J. Org. Chem.* 1992, 57, 5947-5955.
Hotamisligil, G. S.; Shargill, N. S.; Spiegelman, B. M. et al., *Science* 1993, 259, 87-91.
Nigel RA Beeley; Phillip RJ Ansell; Andrew JP Docherty; *Curr. Opin. Ther. Patents* (1994) 4(1); 7-16.
Packer, M. *Circulation*, 1995, 92(6), 1379-1382.
Ferrari, R.; Bachetti, T. et al. *Circulation*, 1995, 92(6), 1479-1486.
Pallares-Trujillo, J.; Lopez-Soriano, F. J. Argiles, *J. M. Med. Res. Reviews*, 1995. 15(6), 533-546.
Rankin, E. C.; Choy, E. H.; Kassimos, D.; Kingsley, G. H.; Sopwith, A. M.; Isenberg, D. A.; Panayl, G. S. Br. *J. Rheumatol*, 1995, 34, 334-342.
J.R. Morphy; T.A. Millican; J.R. Porter; *Curr. Medicinal. Chem.* (1995) 2: 743-762.

John R. Porter, T. Andrew Millican; J. Richard Morphy; Recent Developments in Matrix Metalloproteinase Inhibitors; *Exp. Opin. Ther. Patents*, (1995) 5 (12): 1287-1296.
Peter Steele; *Exp. Opin. Ther. Patents* (1995) 5(2) 99-110.
Pharmaprojects, 1996 Therapeutic Updates 17 (Oct.) au197-M2Z.
Gerard M. McGreehan; Joanne Uhl; *Current Pharmaceutical Design*, 1996, 2, 662-667.
Recent Advances in Matrix Metalloproteinase Inhibitor Research, R. P. Beckett, A. H. Davidson, A. H. Drummon, P. Huxley and M. Whittaker, *Drug Discovery Today*, (Research Focus), vol. 1, 16-26 (1996).
Grossman, J. M.; Brahn, E. *J. Women's Health* 1997, 6(6), 627-638.
Isomaki, P.; Punnonen, *J. Ann. Med.* 1997, 29, 499-507.
MacPherson, et al. in *J. Med. Chem.*, 1997, 40, 2525-2532.
Shire, M.G.; Muller, G. W. *Exp. Opin.* Ther. Patents 1998, 8(5), 531-544.
Camussi, G., Lupia, E. *Drugs*, 1998, 55(5), 613-620.
Ksontini, R.; MacKay, S.L. D.; Moldawer, L. L. *Arch. Surg.* 1998, 133, 558-567.
R Paul Beckett; Mark Whittaker; *Exp. Opin. Ther. Patents* (1998) 8(3); 259-281.
*Scrip.* 1998, 2349, 20.
Tamura, et al. in *J. Med. Chem.* 1998, 41, 640-649.
Levin, J. I. ; DiJoseph, J. F.; Killar, L. M.; Sung, A.; Walter, T.; M. A.; Roth, C. E.; Skotnicki, J. R., Albright, J. D. *Bioorg. & Med. Chem. Lett.* 1998, 8, 2657-2662.
Pikul, S.; McDow, Dunham, K. L.; Almstead, N. G.; De, B.; Natchus, . G.; Anastasio, M.V. McPhail, S. J.; Snider, C. E. ; Taiwo, Y. O.; Rydel, T.; Dunaway, C. M.; Gu, F., Mieling, G. E. *J. Med. Chem.* 1998, 41, 3568-3571.
Clements, John M. et al., "Matrix metalloproteinase expression during experimental autoimmune encephalomyelitis and effects of a combined matrix metalloproteinase and tumour necrosis factor-α inhibitor", J. of Neuro. 74 (1997) 85-94.
Colon, A.L. et al., "Implication of TNF-α Convertase (TACE/ADAM17) in Inducible Nitric Oxide Synthase Expression and Inflammation in an Experimental Model and Colitis", Cytokine, (2001), 16(6):220-226.
Duffy, Michael J. et al., "The ADAM's family of proteins: from basic studies to potential clinical applications", Thromb Haemost (2003); 89:622-31.
Feldman, Arthur M. et al., "The Role of Tumor Necrosis Factor in the Pathophysiology of Heart Failure", J. Am. Col. Cardio., 2000; 35(3):537-544.
Gilles, Stefanie et al., "Release of TNF-α during myocardial reperfusion depends on oxidative stress and its prevented by mast cell stabilizers", Cardio. Research, 60 (2003) 608-616.
Hotamisligil, Gokhan S. et al., "Tumor Necrosis Factor-α: A Key Component of the Obesity-Diabetes Link", Diabetes, (1994) 43:1271-1278.
Kirkegaard, T. et al., "Tumour necrosis factor-α converting enzyme (TACE) activity in human colonic epithelial cells", Clin. Exp. Immunol., 2004, 135:146-153.
Kristensen et al., "Localization of tumour necrosis factor-alpha (TNF-alpha) and its receptors in normal and psoriatic skin: epidermal cells express the 55-kD but not the 75-kD TNF receptor," Clin. Exp. Immunol. (1993) Nov;94(2):354-62.
Lowe, Christopher, "Tumour necrosis factor-alpha antagonists and their therapeutic applications", Exp. Opin. Ther. Patents (1998) 8(10):1309-1322.
Morimoto, Yasuo et al., "KB-R7785, A Novel Matrix metalloproteinase Inhibitor, Exerts its Antidiabetic Effect by Inhibiting Tumor Necrosis Factor-α Production", Life Sciences, (1997), 61(8):795-803.
Moro, Maria A. et al., "Expression and Function of Tumour Necrosis Factor-α Converting Enzyme in the Central Nervous System", Neurosignals (2003); 12:53-58.
Nelson et al., "Matrix metalloproteinases: biologic activity and clinical implications," J. Clin. Oncol. (2000) ;18(5):1135-49.
Newton, R.C. et al, "Biology of TACE inhibition", Ann. Rheum. Dis. (2001); 60:iii25-iii32.

Newton, Robert C. et al., "Therapeutic Potential and Strategies for Inhibiting Tumor Necrosis Factor-alpha", J. Med. Chem., vol. 42, No. 13 (1999) 2295-2314.

Peterson, J. Thomas, "Matrix Metallopteinase Inhibitor Development and the Remodeling of Drug Discovery", Heart Failure Reviews, (2004); 9:63-79.

Reimold, A.M., "TNF-alpha as Therapeutic Target: New Drugs, More Applications", Current Drug Targets —Inflammation & Allergy, (2002); 1:77-392.

Renkiewicz, Richard et al., "Broad-Spectrum Matrix Metallopoteinase Inhibitor Marimastat-Induced Musculoskeletal Side Effects in Rats", Arthritis & Rheumatism, vol. 48, No. 6, Jun. 2003; 1742-1749.

Robertshaw, H.J. et al., "Release of tumour necrosis factor-alpha (TNFα) by TNFα cleaving enzyme (TACE) in response to septic stimuli in vitro", Brit. J. Anaesth., 2005, 94(2):222-228.

Rutgeerts, R. et al., "Novel Therapies for Crohn's Disease", Drugs of Today (2000);36(Suppl. G): 59-68.

Satoh, Manoru et al., "Increased expression of tumor necrosis factor-α converting enzyme and tumor necrosis factor-α in peripheral blood mononuclear cells in patients with advanced congestive heart failure", Euro. J. Heart Failure 6 (2004) 869-875.

Skotnicki, Jerauld S. et al., "TNF-alpha Converting Enzyme (TACE) as a Therapeutic Target", Med. Chem., 2003, 153-162.

Van Assche, Gert et al., "Anti-TNF agents in Crohn's disease", Exp. Opin. Invest. Drugs (2000) 9(1);103-111.

\* cited by examiner

ALLENIC ARYL SULFONAMIDE HYDROXAMIC ACIDS AS MATRIX METALLOPROTEINASE AND TACE INHIBITORS

CROSS REFERENCE TO RELATED APPLICATIONS

"This application claims priority from copending provisional application Ser. No. 60/336,050 filed on Nov. 1, 2001, the entire disclosure of which is hereby incorporated by reference."

FIELD OF INVENTION

This invention relates to allenic aryl sulfonamide hydroxamic acids which act as inhibitors of TNF-α converting enzyme (TACE) and matrix metalloproteinase (MMP). The compounds of the present invention are useful in disease conditions mediated by MMP and TACE, such as rheumatoid arthritis, osteoarthritis, sepsis, AIDS, ulcerative colitis, multiple sclerosis, Crohn's disease, degenerative cartilage loss, graft rejection, cachexia, inflammation, fever, insulin resistance, septic shock, congestive heart failure, inflammatory disease of the central nervous system, inflammatory bowel disease and HIV.

BACKGROUND OF THE INVENTION

TNF-α converting enzyme (TACE) catalyzes the formation of TNF-α from membrane bound TNF-α precursor protein. TNF-α is a pro-inflammatory cytokine that is believed to have a role in rheumatoid arthritis [Shire, M. G.; Muller, G. W. *Exp. Opin. Ther. Patents* 1998, 8(5), 531; Grossman, J. M.; Brahn, E. *J. Women's Health* 1997, 6(6), 627; Isomaki, P.; Punnonen, *J. Ann. Med.* 1997, 29, 499; Camussi, G.; Lupia, E. *Drugs*, 1998, 55(5), 613.] septic shock [Mathison, et. al. *J. Clin. Invest.* 1988, 81, 1925; Miethke, et. al. *J. Exp. Med.* 1992, 175, 91.], graft rejection [Piguet, P. F.; Grau, G. E.; et. al. *J. Exp. Med.* 1987, 166, 1280.], cachexia [Beutler, B.; Cerami, A. *Ann. Rev. Biochem.* 1988, 57, 505.], anorexia, inflammation [Ksontini, R,; MacKay, S. L. D.; Moldawer, L. L. *Arch. Surg.* 1998, 133, 558.], congestive heart failure [Packer, M. *Circulation*, 1995, 92(6), 1379; Ferrari, R.; Bachetti, T.; et. al. *Circulation*, 1995, 92(6), 1479.], post-ischaemic reperfusion injury, inflammatory disease of the central nervous system, inflammatory bowel disease, insulin resistance [Hotamisligil, G. S.; Shargill, N. S.; Spiegelman, B. M.; et. al. *Science*, 1993, 259, 87.] and HIV infection [Peterson, P. K.; Gekker, G.; et. al. *J. Clin. Invest.* 1992, 89, 574; Pallares-Trujillo, J.; Lopez-Soriano, F. J. Argiles, J. M. *Med. Res. Reviews*, 1995, 15(6), 533.]], in addition to its well-documented antitumor properties [Old, L. *Science*, 1985, 230, 630.]. For example, research with anti-TNF-α antibodies and transgenic animals has demonstrated that blocking the formation of TNF-α inhibits the progression of arthritis [Rankin, E. C.; Choy, E. H.; Kassimos, D.; Kingsley, G. H.; Sopwith, A. M.; Isenberg, D. A.; Panayi, G. S. *Br. J. Rheumatol.* 1995, 34, 334; *Pharmaprojects*, 1996, Therapeutic Updates 17 (October), au197-M2Z.]. This observation has recently been extended to humans as well as described in "TNF-α in Human Diseases", *Current Pharmaceutical Design*, 1996, 2, 662.

Matrix metalloproteinases (MMPs) are a group of enzymes that have been implicated in the pathological destruction of connective tissue and basement membranes. These zinc containing endopeptidases consist of several subsets of enzymes including collagenases, stromelysins and gelatinases. Of these classes, the gelatinases have been shown to be the MMPs most intimately involved with the growth and spread of tumors. It is known that the level of expression of gelatinase is elevated in malignancies, and that gelatinase can degrade the basement membrane which leads to tumor metastasis. Angiogenesis, required for the growth of solid tumors, has also recently been shown to have a gelatinase component to its pathology. Furthermore, there is evidence to suggest that gelatinase is involved in plaque rupture associated with atherosclerosis. Other conditions mediated by MMPs are restenosis, MMP-mediated osteopenias, inflammatory diseases of the central nervous system, skin aging, tumor growth, osteoarthritis, rheumatoid arthritis, septic arthritis, corneal ulceration, abnormal wound healing, bone disease, proteinuria, aneurysmal aortic disease, degenerative cartilage loss following traumatic joint injury, demyelinating diseases of the nervous system, cirrhosis of the liver, glomerular disease of the kidney, premature rupture of fetal membranes, inflammatory bowel disease, periodontal disease, age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neo-vascularization and corneal graft rejection. For recent reviews, see: (1) Recent Advances in Matrix Metalloproteinase Inhibitor Research, R. P. Beckett, A. H. Davidson, A. H. Drummond, P. Huxley and M. Whittaker, Research Focus, Vol. 1, 16-26, (1996), (2) Curr. Opin. Ther. Patents (1994) 4(1): 7-16, (3) Curr. Medicinal Chem. (1995) 2: 743-762, (4) Exp. Opin. Ther. Patents (1995) 5(2): 1087-110, (5) Exp. Opin. Ther. Patents (1995) 5(12): 1287-1196: (6) Exp. Opin. Ther. Patents (1998) 8(3): 281-259.

It is expected that small molecule inhibitors of TACE would have the potential for treating a variety of disease states. Although a variety of TACE inhibitors are known, many of these molecules are peptidic and peptide-like which suffer from bioavailability and pharmacokinetic problems. In addition, many of these molecules are non-selective, being potent inhibitors of matrix metalloproteinases and, in particular, MMP-1. Inhibition of MMP-1 (collagenase 1) has been postulated to cause joint pain in clinical trials of MMP inhibitors [*Scrip*, 1998, 2349, 20] Long acting, selective, orally bioavailable non-peptide inhibitors of TACE would thus be highly desirable for the treatment of the disease states discussed above.

U.S. Pat. Nos. 5,455,258, 5,506,242, 5,552,419, 5,770,624, 5,804,593, and 5,817,822 as well as European patent application EP606,046A1 and WIPO international publications WO9600214 and WO9722587 disclose non-peptide inhibitors of matrix metalloproteinases and/or TACE of which the aryl sulfonamide hydroxamic acid shown below is representative. Additional publications disclosing sulfonamide based MMP inhibitors which are variants of the sulfonamide-hydroxamate shown below, or the analogous sulfonamide-carboxylates, are European patent applications EP-757037-A1 and EP-757984-A1 and WIPO international publications WO9535275, WO9535276, WO9627583, WO9719068, WO9727174, WO9745402, WO9807697, WO9831664, WO9833768, WO9839313, WO9839329, WO9842659 and WO9843963. The discovery of this type of MMP inhibitor is further detailed by MacPherson, et. al. in *J. Med. Chem.*, 1997, 40, 2525 and Tamura, et al., in *J. Med. Chem.* 1998, 41, 640.

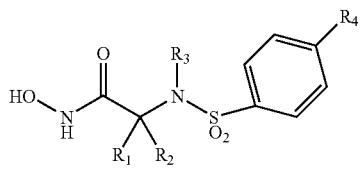

Publications disclosing β-sulfonamide-hydroxamate inhibitors of MMPs and/or TACE in which the carbon alpha to the hydroxamic acid has been joined in a ring to the sulfonamide nitrogen, as shown below, include U.S. Pat. No. 5,753,653, WIPO international publications WO9633172, WO9720824, WO9827069, WO9808815, WO9808822, WO9808823, WO9808825, WO9834918, WO9808827, Levin, et. al. *Bioorg. & Med. Chem. Letters* 1998, 8, 2657 and Pikul, et. al. *J. Med. Chem.* 1998, 41, 3568.

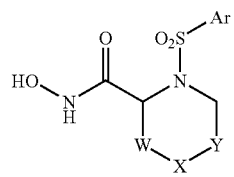

The patent applications DE19,542,189-A1, WO9718194, and EP803505 disclose additional examples of cyclic sulfonamides as MMP and/or TACE inhibitors. In this case the sulfonamide-containing ring is fused to a aromatic or heteroaromatic ring.

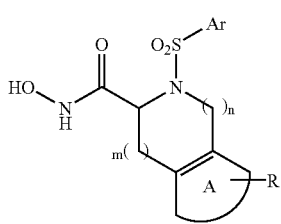

Examples of sulfonamide hydroxamic acid MMP/TACE inhibitors in which a 2 carbon chain separates the hydroxamic acid and the sulfonamide nitrogen, as shown below, are disclosed in WIPO international publications WO9816503, WO9816506, WO9816514 and WO9816520.

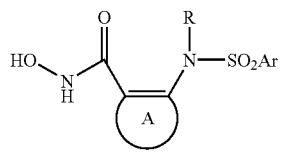

Analogous to the sulfonamides are the phosphinic acid amide hydroxamic acid MMP/TACE inhibitors, exemplified by the structure below, which have been disclosed in WIPO international publication WO9808853.

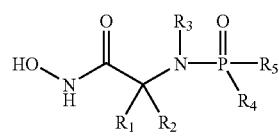

Sulfonamide MMP/TACE inhibitors in which a thiol is the zinc chelating group, as shown below, have been disclosed in WIPO international application 9803166.

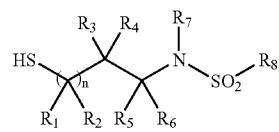

It is an object of this invention to provide aryl sulfonamide hydroxamic acid MMP/TACE inhibitors in which the sulfonyl aryl group is para-substituted with a substituted allenic moiety.

SUMMARY OF THE INVENTION

The invention provides TACE and MMP inhibitors of Formula (I):

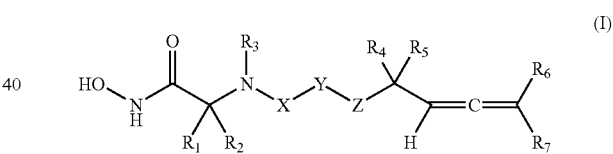

wherein:

X is —S—, —SO—, —SO$_2$— or —P(O)—R$_8$;

Y is aryl or heteroaryl, with the proviso that X and Z may not be bonded to adjacent atoms of Y;

Z is —O—, —NH—, —CH$_2$— or —S—;

R$_1$ is hydrogen, aryl, heteroaryl, C$_5$-C$_8$ cycloheteroalkyl, alkyl of 1 to 6 carbon atoms, alkenyl of 2 to 6 carbon atoms, or alkynyl of 2 to 6 carbon atoms;

R$_2$ is hydrogen, aryl, heteroaryl, cycloalkyl of 3 to 6 carbon atoms, C$_5$-C$_8$ cycloheteroalkyl, alkyl of 1 to 6 carbon atoms, alkenyl of 2 to 6 carbon atoms, or alkynyl of 2 to 6 carbon atoms;

R$_1$ and R$_2$, taken together with the atoms to which they are attached, may form a 3 to 7 membered cycloalkyl or cycloheteroalkyl ring, which are as herein below defined;

R$_3$ is hydrogen, cycloalkyl of 3 to 6 carbon atoms, alkyl of 1 to 6 carbon atoms, alkenyl of 2 to 6 carbon atoms, or alkynyl of 2 to 6 carbon atoms;

or R$_1$ and R$_3$, together with the atoms to which they are attached, may form a 5 to 8 membered ring wherein R$_1$ and R$_3$ represent divalent moieties of the formulae:

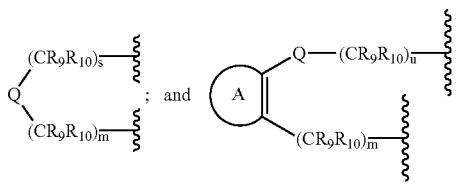

A is aryl or heteroaryl;
Q is a C—C single or double bond, —O—, —S—, —SO—, —SO$_2$—, —NR$_{11}$, or —CONR$_{12}$;
s is an integer of 0 to 3;
u is an integer of 1 to 4;
m is an integer of 1 to 3;
R$_4$ and R$_5$ are each, independently, hydrogen or alkyl of 1 to 6 carbon atoms;
R$_6$ and R$_7$ are each, independently, hydrogen, alkyl of 1 to 6 carbon atoms, cycloalkyl of 3 to 6 carbon atoms, aryl, heteroaryl or C$_5$-C$_8$-cycloheteroalkyl;
or R$_6$ and R$_7$, together with the atom to which they are attached, may form 3 to 7 membered cycloalkyl or cycloheteroalkyl ring;
R$_8$ is alkyl of 1 to 6 carbon atoms, cycloalkyl of 3 to 6 carbon atoms, aryl or heteroaryl;
R$_9$ and R$_{10}$ are each, independently, selected from H, —OR$_{13}$, —NR$_{13}$R$_{14}$, alkyl of 1 to 6 carbon atoms, alkenyl of 2 to 6 carbon atoms, alkynyl of 2 to 6 carbon atoms, cycloalkyl of 3 to 6 carbon atoms, aryl, heteroaryl, —COOR$_{13}$; or —CONR$_{13}$R$_{14}$; or R$_9$ and R$_{10}$ taken together form a C$_3$-C$_6$-cycloalkyl of 3 to 6 carbon atoms or a C$_5$-C$_8$-cycloheteroalkyl ring; or R$_9$ and R$_{10}$ taken together with the carbon to which they are attached, form a carbonyl group;
R$_{11}$ is hydrogen, alkyl of 1 to 6 carbon atoms, cycloalkyl of 3 to 6 carbon atoms, cycloheteroalkyl of 3 to 6 carbon atoms, aryl, heteroaryl, —S(O)$_n$R$_{13}$, —COOR$_{13}$, —CONR$_{13}$R$_{14}$, —SO$_2$NR$_{13}$R$_{14}$ or —COR$_{13}$, and n is an integer of 0 to 2;
R$_{12}$ is hydrogen, aryl, heteroaryl, alkyl of 1 to 6 carbon atoms or cycloalkyl of 3 to 6 carbon atoms; and
R$_{13}$ and R$_{14}$ are each, independently, hydrogen, alkyl of 1 to 6 carbon atoms, cycloalkyl of 3 to 6 carbon atoms, aryl, heteroaryl or C$_5$-C$_8$-cycloheteroalkyl;
or a pharmaceutically acceptable salt thereof.

DESCRIPTION OF THE PREFERRED EMBODIMENTS

Preferred compounds of this invention are those of Formula (I) in which Y is a phenyl ring substituted at the 1- and 4-positions by X and Z, respectively, or a pharmaceutically acceptable salt thereof.

More preferred compounds of this invention are those of Formula (I) in which Y is a phenyl ring substituted at the 1- and 4-positions by X and Z, respectively, X is SO$_2$, or a pharmaceutically acceptable salt thereof.

More preferred compounds of this invention are those of Formula (I) in which Y is a phenyl ring substituted at the 1- and 4-positions by X and Z, respectively, X is SO$_2$, Z is oxygen.

More preferred compounds of this invention are those of Formula (I) in which Y is a phenyl ring substituted at the 1- and 4-positions by X and Z, respectively, X is SO$_2$, Z is oxygen and R$_4$, R$_5$, and R$_6$ are hydrogen.

More preferred compounds of this invention are those of Formula (I) in which Y is a phenyl ring substituted at the 1- and 4-positions by X and Z, respectively, X is SO$_2$, Z is oxygen, R$_4$, R$_5$, and R$_6$ are hydrogen, and R$_7$ is H or methyl.

More preferred compounds of this invention are those of Formula (I) in which Y is a phenyl ring substituted at the 1- and 4-positions by X and Z, respectively, X is SO$_2$, Z is oxygen, R$_2$, R$_4$, R$_5$, and R$_6$ are hydrogen, and R$_7$ is H or methyl, R$_1$ and R$_3$, together with the atoms to which they are attached, form a thiomorpholine ring.

More preferred compounds of this invention are those of Formula (I) in which Y is a phenyl ring substituted at the 1- and 4-positions by X and Z, respectively, X is SO$_2$, Z is oxygen, R$_2$, R$_4$, R$_5$, and R$_6$ are hydrogen, and R$_7$ is H or methyl, R$_1$ and R$_3$, together with the atoms to which they are attached, form a thiomorpholine ring such that Formula (I) has the absolute stereochemistry shown above, or a pharmaceutically acceptable salt thereof.

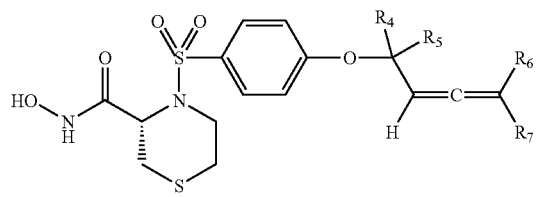

More preferred compounds of this invention are those of Formula (I) in which Y is a phenyl ring substituted at the 1- and 4-positions by X and Z, respectively, X is SO$_2$, Z is oxygen, R$_4$, R$_5$, and R$_6$ are hydrogen, R$_7$ is H or methyl, and R$_3$ is H or methyl.

More preferred compounds of this invention are those of structure Formula (I) in which Y is a phenyl ring substituted at the 1- and 4-positions by X and Z, respectively, X is SO$_2$, Z is oxygen, R$_4$, R$_5$, and R$_6$ are hydrogen, R$_7$ and R$_3$ is H or methyl, and R$_2$ is isopropyl as shown below.

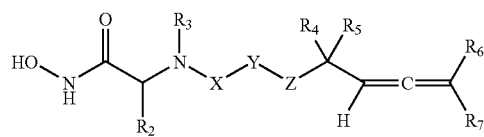

More preferred compounds of this invention are those of Formula (I) in which Y is a phenyl ring substituted at the 1- and 4-positions by X and Z, respectively, X is SO$_2$, Z is oxygen, R$_4$, R$_5$, and R$_6$ are hydrogen, R$_7$ and R$_3$ is H or methyl, R$_2$ is isopropyl, and R$_1$ is hydrogen, such that these compounds have the D-configuration, as shown below:

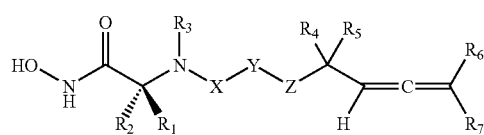

Among the specifically preferred compounds of this invention according to Formula (I) are the following compounds or pharmaceutically acceptable salts thereof:
2-({[4-(2,3-Butadienyloxy)phenyl]sulfonyl}amino)-N-hydroxy-3-methylbutanamide, 2-[{[4-(2,3-Butadienyloxy)phenyl]sulfonyl}(methyl)
  amino]-N-hydroxy-3-methylbutanamide,
N-Hydroxy-3-methyl-2-({[4-(2,3-pentadienyloxy)phenyl]
  sulfonyl}amino)butanamide,
N-Hydroxy-3-methyl-2-(methyl{[4-(2,3-pentadienyloxy)
  phenyl]sulfonyl}amino)butanamide,
(3S)-4-{[4-(2,3-Butadienyloxy)phenyl]sulfonyl}-N-hy-
  droxy-2,2-dimethyl-3-thiomorpholinecarboxamide,
(3S)-N-Hydroxy-2,2-dimethyl-4-{[4-(2,3-pentadienyloxy)
  phenyl]sulfonyl}-3-thiomorpholinecarboxamide,
1-Acetyl-4-{[4-(2,3-butadienyloxy)phenyl]sulfonyl}-N-hy-
  droxy-2,3,4,5-tetrahydro-1H-1,4-benzodiazepine-3-car-
  boxamide,
1-Benzoyl-4-(4-buta-2,3-dienyloxy-benzenesulfonyl)-2,3,4,
  5-tetrahydro-1H-benzo[e][1,4]diazepine-3-carboxylic
  acid hydroxyamide and
1-Benzoyl-N-hydroxy-4-{[4-(2,3-pentadienyloxy)phenyl]
  sulfonyl}-2,3,4,5-tetrahydro-1H-1,4-benzodiazepine-3-
  carboxamide.

Heteroaryl, as used throughout, is a 5 to 10 membered mono- or bicyclic ring having from 1 to 3 heteroatoms selected from —N—, —$NR_{11}$, —S— and —O—. Heteroaryl is preferably

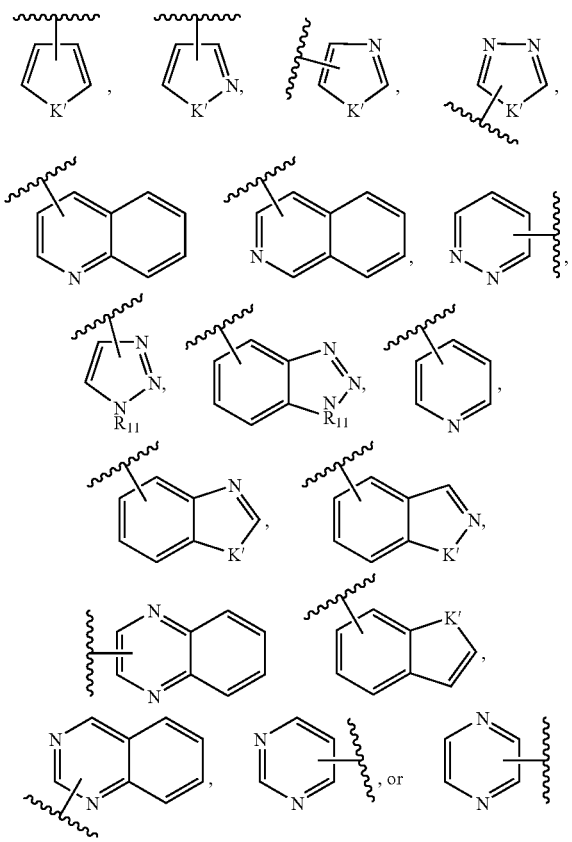

wherein K' is —O—, —S— or —$NR_{11}$ and —$R_{11}$ is as hereinabove defined. Preferred heteroaryl rings include pyrrole, furan, thiophene, pyridine, pyrimidinde, pyridazine, pyrazine, triazole, pyrazole, imidazole, isothiazole, thiazole, isoxazole, oxazole, indole, isoindole, benzofuran, benzothiophene, quinoline, isoquinoline, quinoxazole, quinazole, benzotriazole, indazole, benimidazole, benzothiazole, benzisoxazole, and benzoxazole. Heteroaryl groups may optionally be mono or disubstituted.

$C_5$-$C_8$ cycloheteroalkyl as used herein refers to a 5 to 8 membered saturated or unsaturated mono or bi-cyclic ring having 1 or 2 heteroatoms independently selected from —N—, —$NR_{11}$, —S— or —O—. Heterocycloalkyl rings of the present invention are preferably selected from;

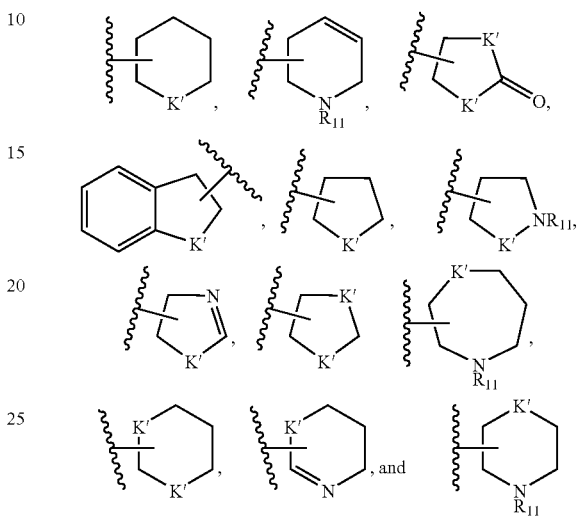

wherein K' is —$NR_{11}$, —O— or —S— and —$R_{11}$ is as hereinabove defined. Preferred heterocycloalkyl rings include piperidine, piperazine, morpholine, tetrahydropyran, tetrahydrofuran or pyrrolidine. Cycloheteroalkyl groups of the present invention may optionally be mono- or disubstituted.

Aryl, as used herein refers to a phenyl or napthyl rings which may, optionally be mono-, di- or tri-substituted.

Alkyl means a straight or branched chain saturated aliphatic hydrocarbon radical of 1 to 6 carbon atoms. Examples include: alkyl group of 1 to 6 carbon atoms such as e.g. methyl, ethyl, propyl, isopropyl, butyl, isobutyl, pentyl or hexyl.

Alkenyl means a branched or unbranched hydrocarbon radical of 2 to 6 carbon atoms containing at least one carbon-carbon double bond, each double bond being independently cis, trans or nongeometric isomer.

Alkynyl means a branched or unbranched hydrocarbon radical having 2 to 6 carbon atoms containing at least one carbon-carbon triple bond.

Perfluoroalkyl means an alkyl group which includes both straight chain as well as branched moieties of 2 to 6 carbon atoms wherein each hydrogen has been replaced by a fluorine atom. An example is trifluoromethyl.

Alkyl, alkenyl, alkynyl and cycloalkyl groups may be unsubstituted (carbons bonded to hydrogen, or other carbons in the chain or ring) or may be mono- or poly-substituted.

Halogen means bromine, chlorine, fluorine, and iodine.

Cycloalkyl denotes a 3 to 6 membered carbocyclic ring such as cyclopropyl, cyclobutyl, cyclopentyl or cyclohexyl.

Suitable substituents of aryl, heteroaryl, alkyl, alkenyl, alkynyl, and cycloalkyl include, but are not limited to hydrogen, halogen, alkyl of 1 to 6 carbon atoms; alkenyl of 2 to 6 carbon atoms; alkynyl of 2 to 6 carbon atoms, cycloalkyl of 3 to 6 carbon atoms, —$OR_8$, —CN, —$COR_8$, perfluoroalkyl of 1 to 4 carbon atoms, —O-perfluoroalkyl of 1 to 4 carbon atoms, —CONR$_{13}$R$_{14}$, —S(O)$_n$R$_{13}$, —OPO(OR$_{13}$)OR$_{14}$, —PO(OR$_{13}$)R$_{14}$, —OC(O)NR$_{13}$R$_{14}$, —C(O)NR$_{13}$OR$_{14}$, —COOR$_{13}$, —SO$_3$H, —NR$_{13}$R$_{14}$, —N[(CH$_2$)$_2$]$_2$NR$_{13}$, —NR$_{13}$COR$_{14}$, —NR$_{13}$COOR$_{14}$, —SO$_2$NR$_{13}$R$_{14}$, —NO$_2$, —N(R$_{13}$)SO$_2$R$_{14}$, —NR$_{13}$CONR$_{13}$R$_{14}$, —NR$_{13}$C(=NR$_{14}$)NR$_{13}$R$_{14}$, —NR$_{13}$C(=NR$_{14}$)N(SO$_2$R$_{13}$)R$_{14}$, NR$_{13}$C(=NR$_{14}$)N(C=OR$_{13}$)R$_{14}$-tetrazol-5-yl, —SO$_2$NHCN, —SO$_2$NHCONR$_{13}$R$_{14}$, phenyl, heteroaryl, or C$_5$-C$_8$-cycloheteroalkyl;

wherein —NR$_{13}$R$_{14}$ may form a pyrrolidine, piperidine, morpholine, thiomorpholine, oxazolidine, thiazolidine, pyrazolidine, piperazine, or azetidine ring; and when a moiety contains more than substituent with the same designation (i.e., phenyl tri-substituted with R$_1$) each of those substituents (R$_1$ in this case) may be the same or different; and R$_8$, R$_{13}$ and R$_{14}$ are as hereinabove defined.

Alkali metal base as used herein means an alkali metal hydroxide, preferably, sodium hydroxide, potassium hydroxide and lithium hydroxide.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains an acidic moiety.

The compounds of this invention may contain an asymmetric carbon atom and some of the compounds of this invention may contain one or more asymmetric centers and may thus give rise to optical isomers and diastereomers. While shown without respect to stereochemistry, the present invention includes such optical isomers and diastereomers; as well as the racemic and resolved, enantiomerically pure R and S stereoisomers; as well as other mixtures of the R and S stereoisomers and pharmaceutically acceptable salts thereof. It is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

The compounds of this invention are shown to inhibit the enzymes MMP-1, MMP-9, MMP-13 and TNF-α converting enzyme (TACE) and are therefore useful in the treatment of arthritis, tumor metastasis, tissue ulceration, abnormal wound healing, periodontal disease, graft rejection, insulin resistance, bone disease and HIV infection. In particular, the compounds of the invention provide enhanced levels of inhibition of the activity of TACE in vitro and in cellular assay and/or enhanced selectivity over MMP-1 and are thus particularly useful in the treatment of diseases mediated by TNF.

In particular, a therapeutically effective amount of a compound of Formula (I) of this invention is useful as a method of treating a pathological condition mediated by TNF-α converting enzyme (TACE) in mammals and useful in the treatment of rheumatoid arthritis, osteoarthritis, sepsis, AIDS, ulcerative colitis, multiple sclerosis, Crohn's disease, degenerative cartilage loss, graft rejection, cachexia, inflammation, fever, insulin resistance, septic shock, congestive heart failure, inflammatory disease of the central nervous system, inflammatory bowel disease or HIV.

Further, a therapeutically effective amount of a compound of Formula (I) of this invention is useful as a method of treating a pathological condition mediated by matrix metalloproteinases in mammals and useful in the treatment of rheumatoid arthritis, osteoarthritis, sepsis, AIDS, ulcerative colitis, multiple sclerosis, Crohn's disease, degenerative cartilage loss, graft rejection, cachexia, inflammation, fever, insulin resistance, septic shock, congestive heart failure, inflammatory disease of the central nervous system, inflammatory bowel disease or HIV.

The invention is further directed to a process for preparing intermediate compounds of the formula

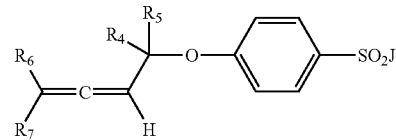

useful for preparing compounds of Formula (I) comprising the steps:

(a) reacting an alkynyl reagent of the formula:

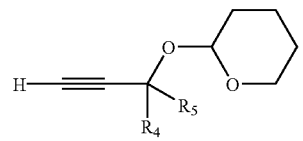

wherein R$_4$ and R$_5$ are as hereinabove defined, with a carbonyl compound of the formula:

wherein R$_6$ and R$_7$ are as hereinabove defined, in the presence of a strong base such as n-BuLi, in the presence of methyl iodide (MeI), and an organic acid such as preferably pyridinium p-toluenesulfonic acid to produce an alcohol of the formula:

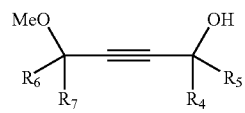

wherein R$_4$, R$_5$, R$_6$, and R$_7$ are as hereinabove defined;

(b) reacting an alcohol of step a above with a hydride reagent such as lithium aluminum hydride (LAH) and in the presence of iodine to produce an allene of the formula:

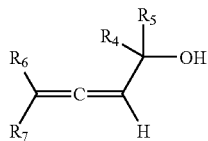

wherein $R_4$, $R_5$, $R_6$, and $R_7$ are as hereinabove defined;

(c) reacting an allene of step b with triphenylphosphine and triphosgene to produce a chloroallene of the formula:

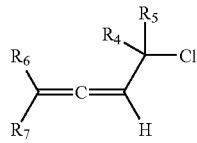

wherein $R_4$, $R_5$, $R_6$, and $R_7$ are as hereinabove defined;

(d) reacting a chloroallene of step c with a sulfonic acid of the formula, or a salt or solvate thereof:

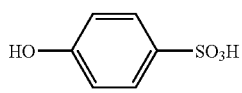

in the presence of an alkali metal base such as preferably sodium hydroxide to produce an ether of formula:

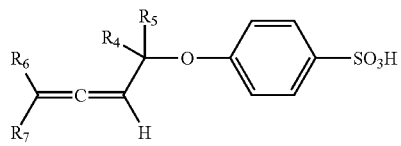

wherein $R_4$, $R_5$, $R_6$, and $R_7$ are as hereinabove defined;

(e) reacting an ether of step d, or a salt or a solvate thereof, with a chlorinating agent such as thionyl chloride, chlorosulfonic acid, oxalyl chloride, or phosphorous pentachloride, or other halogenating agents such as fluorosulfonic acid or thionyl bromide to produce an allene of the formula:

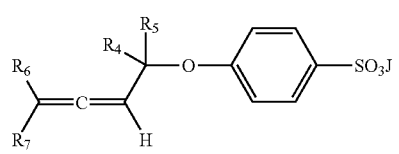

wherein $R_4$, $R_5$, $R_6$, and $R_7$ are as hereinabove defined, and J is F, Cl, or Br.

The invention is further directed to a process for preparing an allene of the formula:

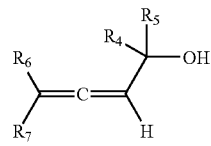

useful for the synthesis of compounds of Formula I, which comprises the steps of (a) reacting an amine of the formula:

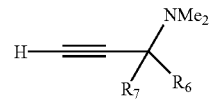

wherein $R_6$ and $R_7$ are as hereinabove defined, with a carbonyl compound of the formula:

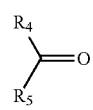

wherein $R_4$ and $R_5$ are as hereinabove defined, in the presence of a strong base such as preferably n-butyllithium, to produce an alcohol of the formula:

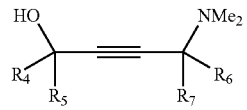

wherein $R_4$, $R_5$, $R_6$, and $R_7$ are as hereinabove defined;

(b) reacting an alcohol of step a, with methyl iodide to produce an alcohol of the formula:

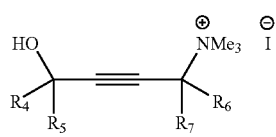

wherein $R_4$, $R_5$, $R_6$, and $R_7$ are as hereinabove defined;

(c) reacting an alcohol of step b, with a hydride reducing agent such as preferably lithium aluminum hydride to produce an allene of the formula:

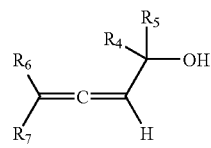

The invention is further directed to a process for preparing an allene of the formula:

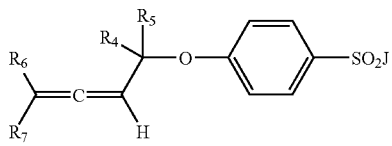

useful for making compounds of Formula I, wherein $R_4$, $R_5$, $R_6$, and $R_7$ are as hereinabove defined and J is F, Cl, or Br, by reacting a phenol of the formula:

wherein J is as hereinabove defined, with an alcohol of the formula,

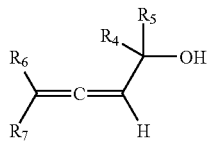

in the presence of triphenyl phosphine, and diethylazodicarboxylate to produce an allene of the formula

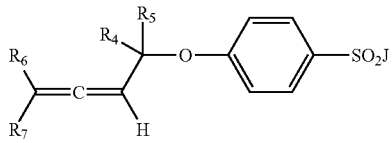

Compounds of the present invention are prepared using conventional techniques known to those skilled in the art. The starting materials used in preparing the compounds of the invention are known, made by known methods as described in the following references or are commercially available.

U.S. Pat. No. 5,753,653; Kogami, Yuji; Okawa, Kenji. *Bull. Chem. Soc. Jpn.* 1987, 60(8), 2963; Auvin, S.; Cochet, O.; Kucharczyk, N.; Le Goffic, F.; Badet, B. *Bioorganic Chemistry*, 1991, 19, 143; Angle, S. R.; Breitenbucher, J. G.; Arnaiz, D. O. *J. Org. Chem.* 1992, 57, 5947; Asher, Vikram; Becu, Christian; Anteunis, Marc J. O.; Callens, Roland *Tetrahedron Lett.* 1981, 22(2), 141; Levin, J. I.; DiJoseph, J. F.; Killar, L. M.; Sung, A.; Walter, T.; Sharr, M. A.; Roth, C. E.; Skotnicki, J. S.; Albright, J. D. *Bioorg. & Med. Chem. Lett.* 1998, 8,2657; U.S. Pat. No. 5,770, 624; Pikul, S.; McDow Dunham, K. L.; Almstead, N. G.; De, B.; Natchus, M. G.; Anastasio, M. V.; McPhail, S. J.; Snider, C. E.; Taiwo, Y. O.; Rydel, T.; Dunaway, C. M.; Gu, F.; Mieling, G. E. *J. Med. Chem.* 1998, 41, 3568; U.S. Pat. Nos. 5,455,258, 5,506,242, 5,552,419 and 5,770,624; MacPherson, et. al. in *J. Med. Chem.*, 1997, 40, 2525; U.S. Pat. Nos. 5,455,258 and 5,552,419; U.S. Pat. No. 5,804,593; Tamura, et. al. in *J. Med. Chem.* 1998, 41, 640.

Those skilled in the art will recognize that certain reactions are best carried out when other potentially reactive functionality on the molecule is masked or protected, thus avoiding undesirable side reactions and/or increasing the yield of the reaction. To this end, those skilled in the art may use protecting groups. Examples of these protecting group moieties may be found in T. W. Greene, P. G. M. Wuts "Protective Groups in Organic Synthesis", $2^{nd}$ Edition, 1991, Wiley & Sons, New York. Reactive side chain functionalities on amino acid starting materials are preferably protected. The need and choice of protecting groups for a particular reaction is known to those skilled in the art and depends on the nature of the functional group to be protected (hydroxy, amino, carboxy, etc.), the structure and stability of the molecule of which the substituent is part and the reaction conditions. In particular, chapter 2 describes protection/ deprotection of hydroxyl groups, chapter 5 describes protection/deprotection of carboxyl groups and chapter 7 describes protection/deprotection of amino groups.

When preparing or elaborating compounds of the invention containing heterocyclic rings, those skilled in the art recognize that substituents on that ring may be prepared before, after or concomitant with construction of the ring. For clarity, substituents on such rings have been omitted from the schemes herein below.

Those skilled in the art will recognize that the nature and order of the synthetic steps presented may be varied for the purpose of optimizing the formation of the compounds of the invention.

Scheme 1

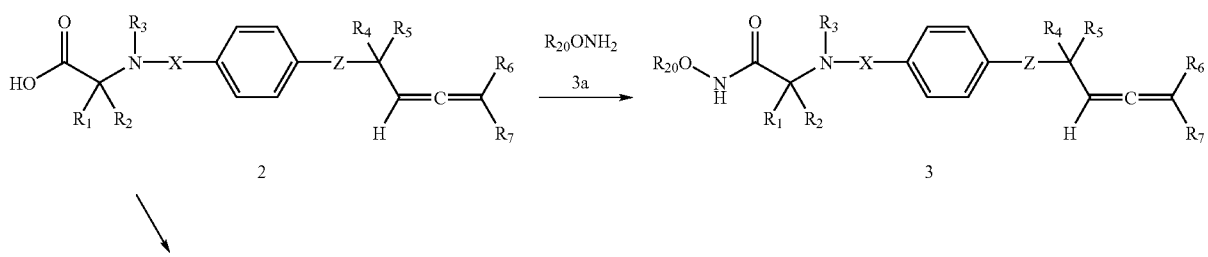

-continued

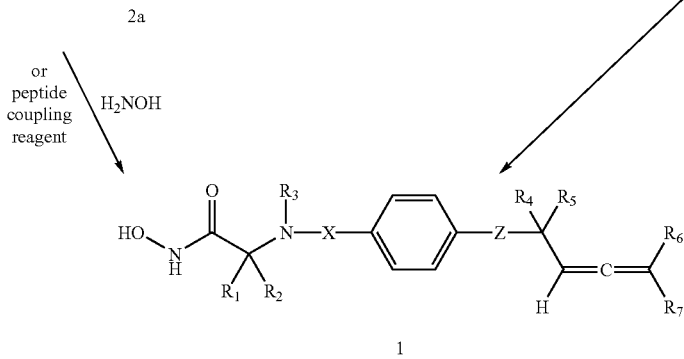

According to Scheme 1, hydroxamic acids 1, of the invention are prepared by converting a carboxylic acid 2, to the corresponding acid chloride, anhydride or mixed anhydride 2a followed by reaction with hydroxylamine. Alternatively, rather than forming the acid chloride, anhydride, or mixed anhydride, reacting carboxylic acid 2 directly with a suitable peptide coupling reagent which include for example, but not limited to N,N'-Dicyclohexylcarbodiimide plus 1-hydroxybenzotriazole; Benzotriazol-1-yloxytris (dimethylamino) phosphonium hexafluorophosphate (BOP-reagent); N,N'-Bis[2-oxo-3-oxazolidinyl]phosphorodiamidic chloride (BOB-Cl); Diphenylphosphinyl chloride (DPP-Cl); Diethoxyphosphoryl cyanide; 2-Chloro-1-methylpyridinium iodide; or Phenyldichlorophosphate plus imidazole followed by reaction with hydroxylamine also gives hydroxamic acids 1. Acid chlorides, anhydrides, mixed anhydrides or peptide coupling reagent products 2a are defined as activating agents. Further, reaction of carboxylic acid 2 with a protected hydroxylamine derivative 3a gives allene 3. Allene 3, wherein $R_{20}$ is a t-butyl, benzyl, tri-alkylsilyl or other suitable masking group, may then be deprotected by known methods which includes treatment with acid to provide the hydroxamic acid 1.

Activating agents 2a are formed by reaction of carboxylic acid 2 with activating reagents which include:

A chlorinating agent such as thionyl chloride, chlorosulfonic acid, oxalyl chloride, or phosphorous pentachloride, or other halogenating agents such as fluorosulfonic acid or thionyl bromide, suitable peptide coupling reagents which include for example, but not limited to N,N'-Dicyclohexylcarbodiimide plus 1-hydroxybenzotriazole; Benzotriazol-1-yloxytris (dimethylamino)phosphonium hexafluorophosphate (BOP-reagent); N,N'-Bis[2-oxo-3-oxazolidinyl] phosphorodiamidic chloride (BOB-Cl); Diphenylphosphinyl chloride (DPP-Cl); Diethoxyphosphoryl cyanide; 2-Chloro-1-methylpyridinium iodide; or Phenyidichlorophosphate plus imidazole; or preparation of a mixed anhydride with ethyl chloroformate.

Carboxylic acids 2 may be prepared as shown in Scheme 2. Amino acid derivative 4, in which $R_{25}$ is hydrogen or a suitable carboxylic acid protecting group, may be sulfonylated or phosphorylated by reacting with allene 6, where J is a suitable leaving group including, but not limited to chlorine. The amino acid derivative 7 may then be alkylated with $R_3J$ 7a and a base such as potassium carbonate or sodium hydride in a polar aprotic solvent such as acetone, N,N-dimethylformamide (DMF), or tetrahydrofuran (THF) to provide protected acid 8. Protected acid 8 is also available through direct reaction of allene 6 with an N-substituted amino acid derivative 5. Conversion of the amino acid derivative 7 or protected acid 8 into the carboxylic acid 2 is performed by acid or base hydrolysis, or other method consistent with the choice of protecting group $R_{25}$ and the presence of an allenic functionality.

Scheme 2

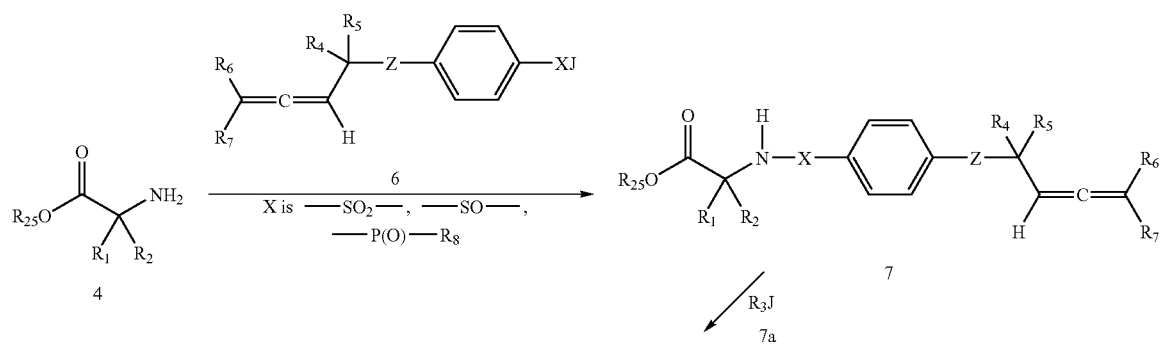

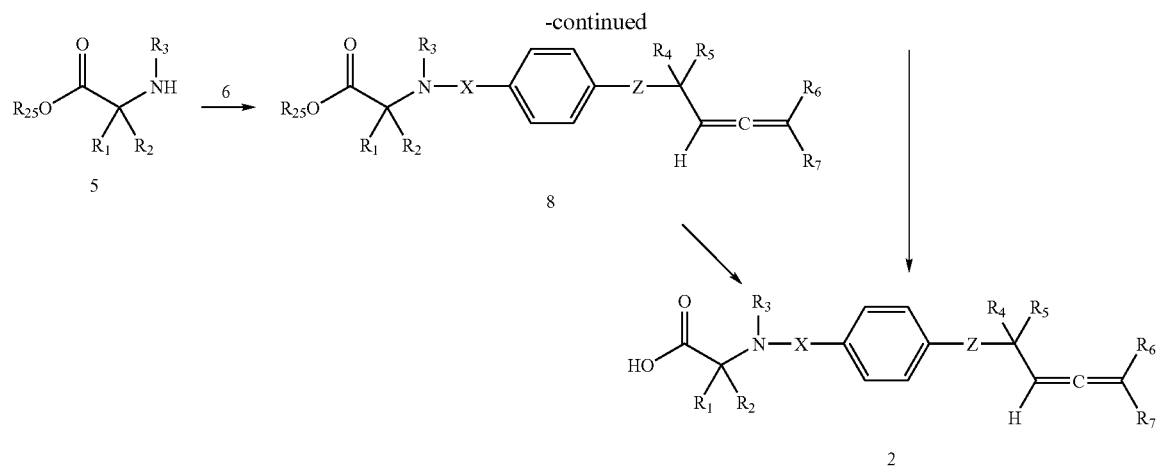

A method of preparation of sulfonyl chloride 12 is shown in Scheme 3. The sulfonic acid salt 9, where $ZR_{30}$ is a hydroxyl, thiol, or substituted amine moiety may be reacted with allenes 10, where J is a suitable leaving group such as halogen, mesylate, tosylate, or triflate (Lathbury, D.; Gallagher, T. *J. Chem. Soc. Chem. Comm.* 1986, 114.: Black, D. K.; Landor, S. R.; Patel, A. N.; Whiter, P. F. *J. Chem. Soc. (C)* 1967, 2260.) to give sulfonic acid salt 11. The sulfonic acid salt 11 can be converted into the corresponding sulfonyl chloride 12 by known methods such as reaction with oxalyl chloride or other reagent compatible with the allenic functionality.

Alternatively, the sulfonic acid salt 9 can be converted into the corresponding sulfonyl chloride, or other sulfonylating agent 13 (Campbell, R. W.; Hill, H. W. *J. Org. Chem.* 1973, 38, 1047.), where $ZR_{30}$ is a hydroxyl group, which can then be treated with an allenic alcohol 14 (Cowie, J. S.; Landor, P. D.; Landor, S. R. *J. Chem. Soc. Perkin I* 1973, 720.: Galanty, E.; Bacso, I.; Coombs, R. V. *Synthesis* 1974, 344: Keck, G. E.; Webb, R. R. *Tetrahedron Lett.* 1982, 23, 3051), where $ZR_{30}$ is a hydroxyl moiety, under Mitsunobu conditions to give sulfonyl chloride 12.

Further, as shown in Scheme 4, phenol or thiophenol 15 where Z is O or S respectively, may be alkylated with allene 10 or allene 14 under basic conditions or Mitsunobu conditions respectively, to give 16, followed by reaction with chlorosulfonic acid to provide sulfonic acid 17. Sulfonic acid 17 can be readily converted to sulfonyl chloride 12 with oxalyl chloride or other suitable reagent.

Scheme 4

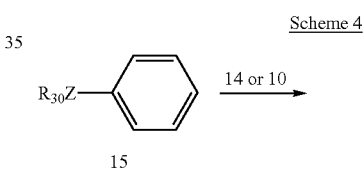

Scheme 3

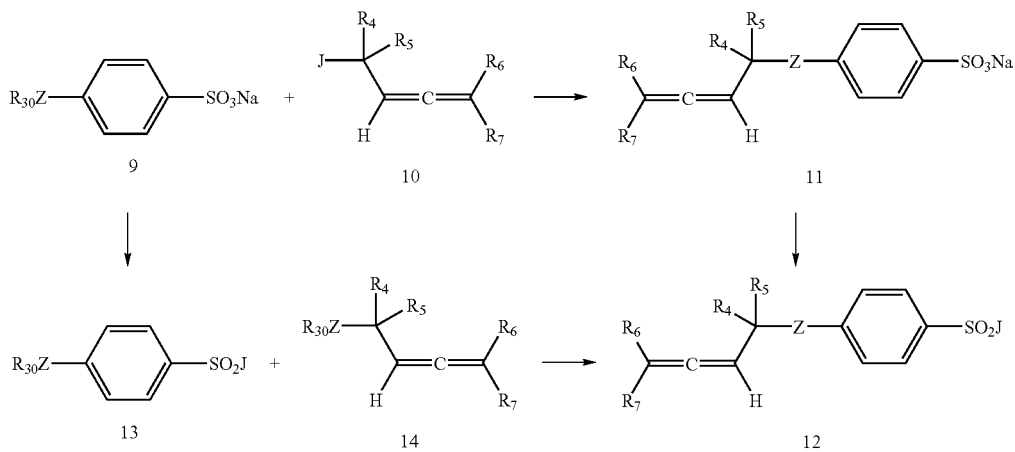

-continued

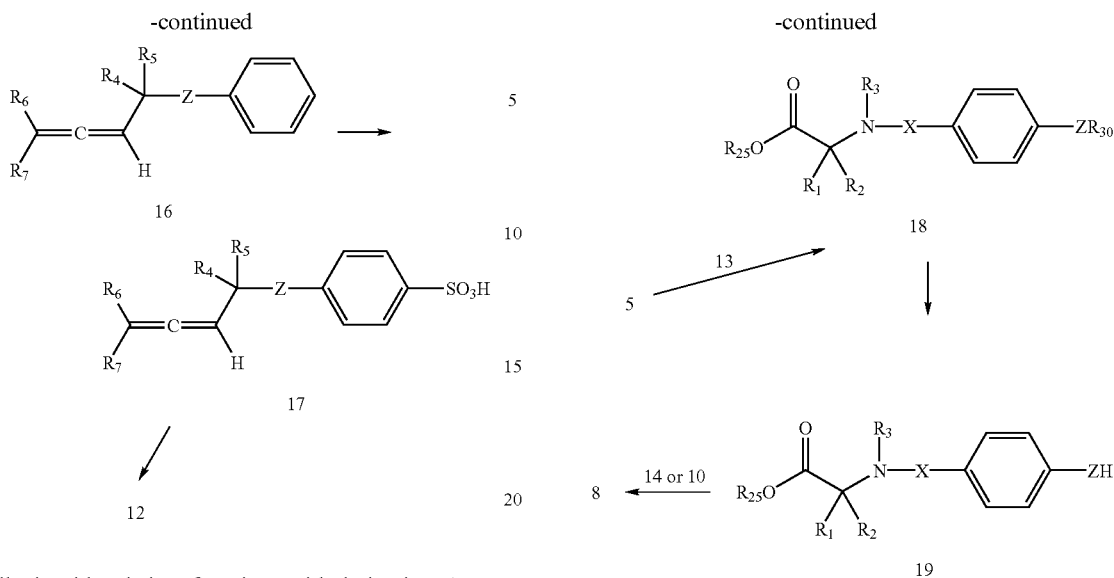

The allenic side chain of amino acid derivative 4 or N-substituted amino acid derivative 5 may be appended as shown in the Scheme 5. Thus, the amino acid derivative 4 or N-substituted amino acid derivative 5 may be sulfonylated with phenol or protected phenol 13, followed by alkylation with $R_3J$ where $ZR_{30}$ is hydroxyl or protected hydroxyl group and X is hereinbefore defined to give protected acid 18. Removal of the protecting group $R_{30}$ provides protected acid 19, which can be alkylated with either allene 10 or 14 to provide protected acid 8.

Scheme 5

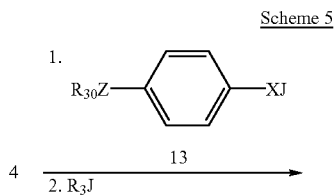

Compounds of the invention in which $R_1$ and $R_3$ together form a thiomorpholine ring may be made according to the Scheme 6. Thiol 20 may be alkylated with disubstituted alkyl 26, where J is a suitable leaving group, under basic conditions to give thiomorpholine 21. Thiomorpholine 21 may be directly sulfonylated with sulfonyl chloride 12 to give sulfone 23, or it can first be sulfonylated with 13 where Z is —O— and X is —SO$_2$— and J is Cl to give thiomorpholine 22 followed by reaction with allene 14 to give sulfone 23 under Mitsunobu conditions. Sulfone 23 may be converted into carboxylic acid 24 by removal of the glocking group $R_{25}$ followed by reaction with hydroxyl amine according to the methods described in Schemes 1 and 2 to afford hydroxamic acid 25.

Scheme 6

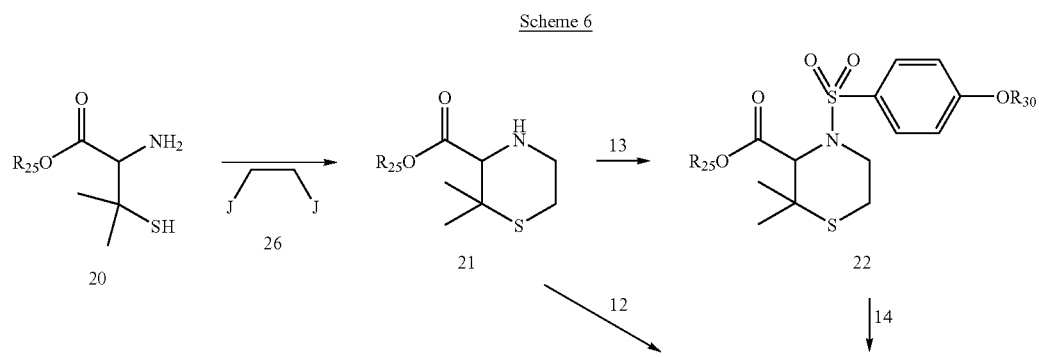

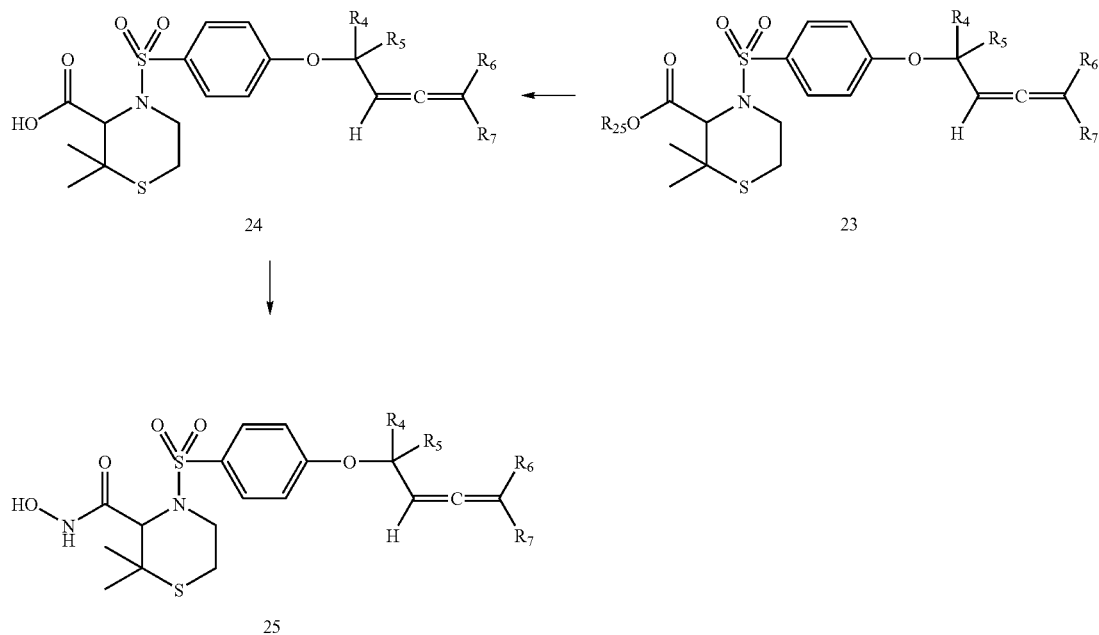

Compounds of the invention in which $R_1$ and $R_3$ taken together form a benzodiazepine ring can be made according to the Scheme 7 (WO200044730). Protected amino acids 26 wherein $R_{40}$ and $R_{41}$, are each H or methyl such as threonine, serine, β-hydroxyvaline, and related derivatives can be converted into the corresponding sulfonamide 28 by reacting with benzenesulfonyl halide 27 in the presence of a base such as triethylamine. The sulfonamide 28 can be alkylated with suitable substituted or unsubstituted 2-nitrobenzyl halides 29 under conditions such as sodium hydride in N,N-dimethylformamide (DMF) to provide the corresponding nitro derivative 31. Reduction under conventional reducing conditions such as catalytic hydrogenation (with Pd/C) or chemical reduction (with $SnCl_2$ or $FeCl_3$) provides N-(2-aminobenzyl)derivative derivative 32. Reaction of N-(2-aminobenzyl)derivative 32 with various acid chlorides and sulfonyl chlorides, in the presence of trialkyl amines or pyridine, provides the dehydro derivative 33. Ring closure of the dehydro derivative 33 to the [1,4]benzodiazepine derivative 34 is carried out by reacting with a mild base such as sodium or potassium bicarbonate in an alcohol solvent such as methanol or ethanol. Deprotecting the blocking group $R_{30}$ of [1,4]benzodiazepine derivative 34, provides phenol 35. Phenol 35 can be alkylated with the allenic alcohol 14 under Mitsunobu conditions as shown in the Schemes 4, 5, and 6 to afford ester derivative 36 which can be converted to sulfone 37 in the presence of lithium hydroxide. Hydroxamic acid derivative 38 is prepared following conditions which include reaction of sulfone 37 with 1-hydroxybenzotriazole (HOBT) and 1-[3-(dimethylamino)propyl]-3-ethylcarbodiimide(DEAC) followed by reaction with hydroxylamine or alternatively conditions as shown in the Scheme 1 and 2.

Scheme 7

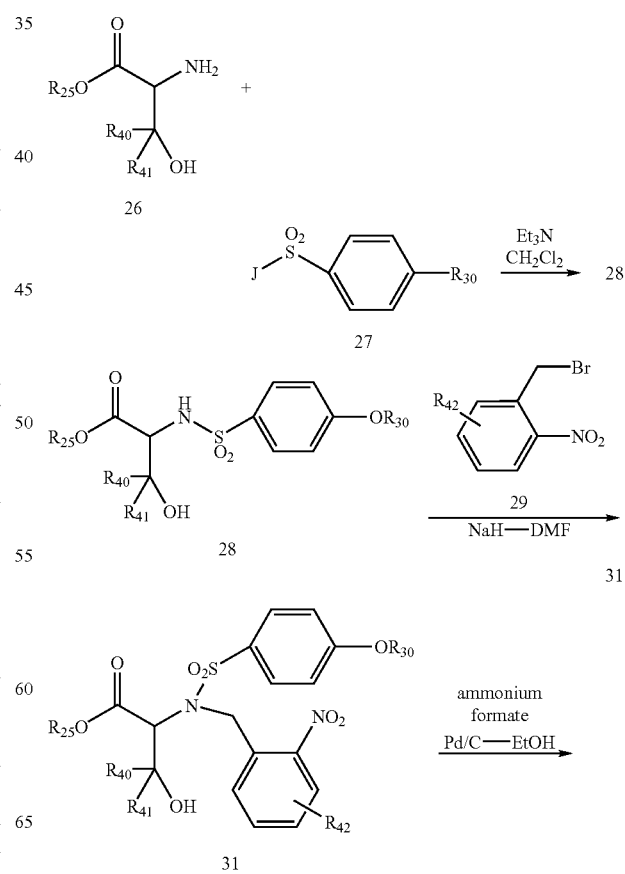

-continued

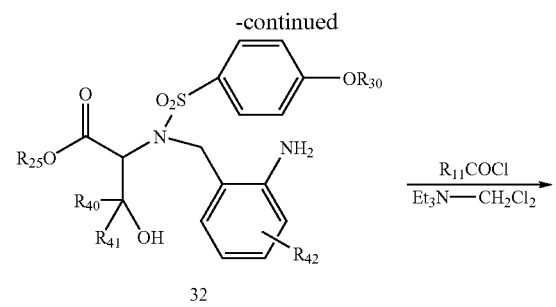

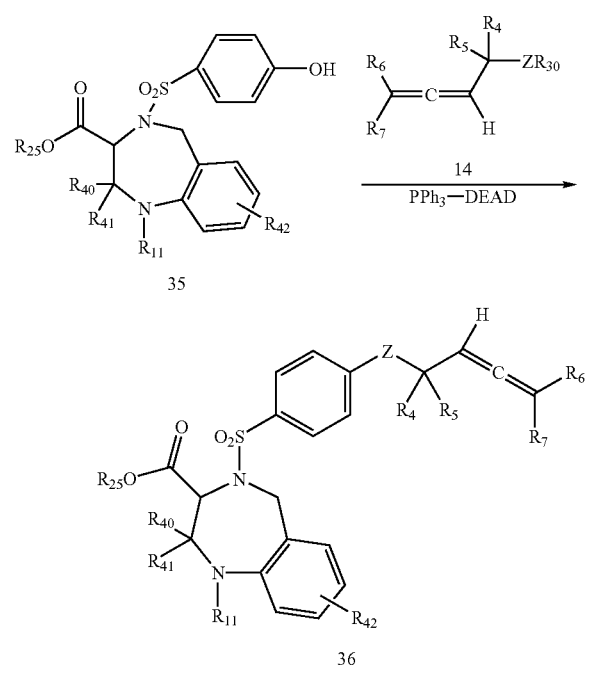

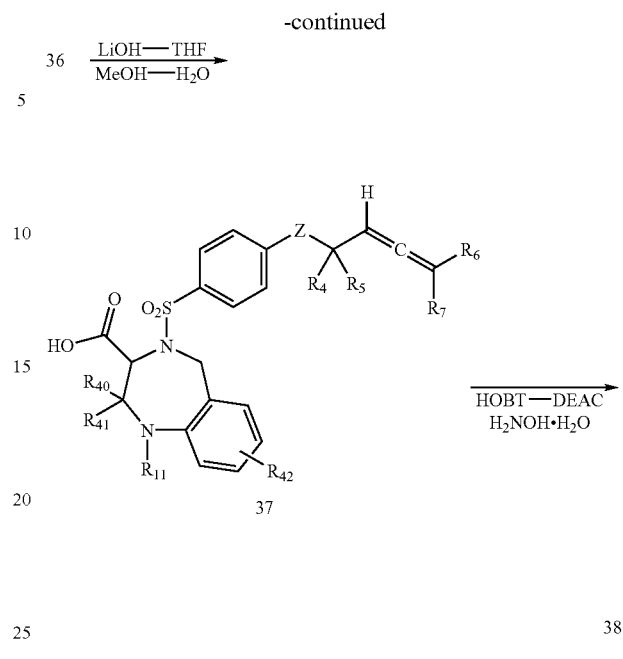

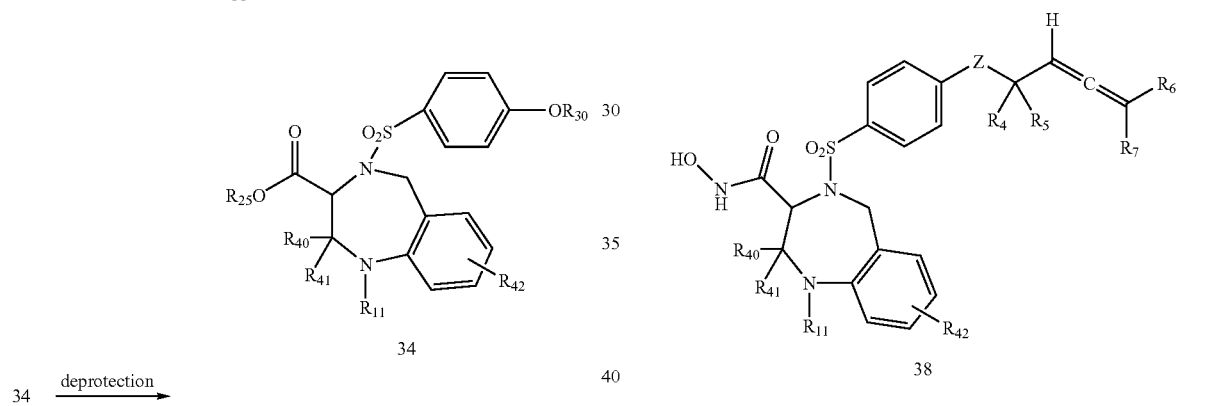

The preparation of intermediate compounds useful in the preparation of compounds of Formula I are outlined in Schemes 8-10.

As shown in Scheme 8, alkynyl reagent 39 where $R_4$ and $R_5$ are hereinbefore defined is reacted with a carbonyl compound 40 where $R_6$ and $R_7$ are hereinbefore defined in the presence of a strong base, preferably butyl lithium, in a solvent such as tetrahydrofuran (THF) and the like in the presence of methyl iodide and and organic acid, preferably pyridinium p-toluenesulfonic acid to give alcohol 41 which is reduced with a hydride reagent, preferably lithium aluminum hydride (LAH) and iodine in a solvent such as tetrahydrofuran and the like to produce an allene 42. Further reaction of allene 42 with triphenylphosphine and triphosgene in a chlorinated hydrocarbon solvent such as methylene chloride and the like affords chloro allene 43 which is further reacted with sulfonic acid 44 in the presence of an alkali metal base, preferably sodium hydroxide to give an ether 45 which is reacted with a chlorinating agent such as thionyl chloride, chlorosulfonic acid, oxalyl chloride, or phosphorous pentachloride or halogenating agent such as fluorosulfonic acid or thionyl bromide in solvents such as acetonitrile and sulfolane to afford allene 46.

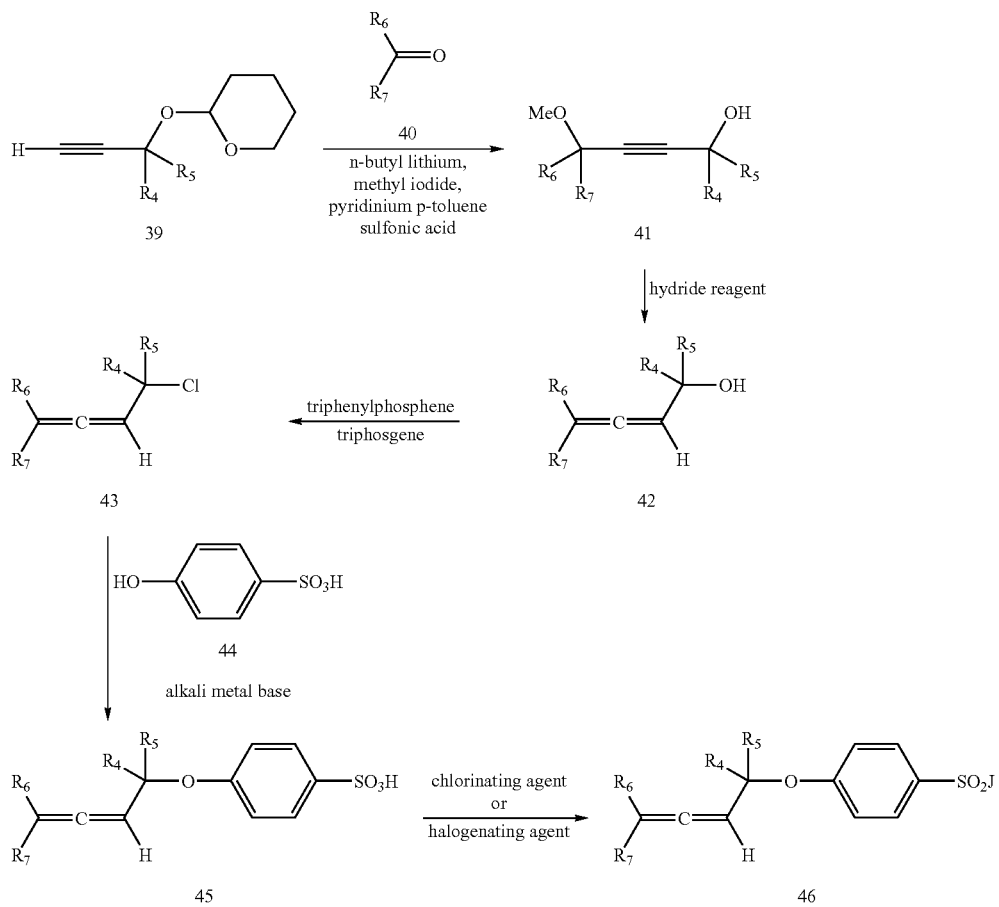

As shown further in Scheme 9, amine 47 where $R_6$ and $R_7$ are hereinbefore defined is reacted with carbonyl compound 48 where R4 and R5 are hereinbefore defined in the presence of a strong base, preferably butyl lithium in solvents such as tetrahydrofuran and the like to afford alcohol 49 which is further reacted with methyl iodide to give alcohol 50 which is reduced with a hydride reducing agent, preferably lithium aluminum hydride in solvents such as tetrahydrofuran and the like to give alcohol 51.

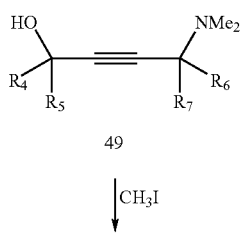

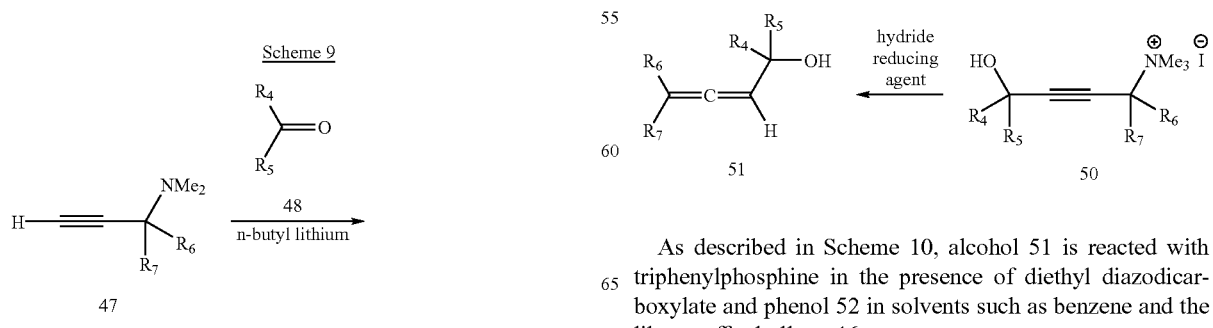

As described in Scheme 10, alcohol 51 is reacted with triphenylphosphine in the presence of diethyl diazodicarboxylate and phenol 52 in solvents such as benzene and the like to afford allene 46.

Scheme 10

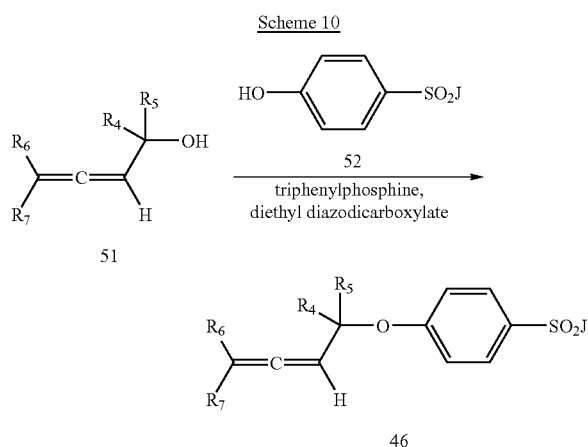

Pharmacology

Standard Pharmacological Test Procedures

Representative compounds of this invention were evaluated as inhibitors of the enzymes MMP-1, MMP-9, MMP-13 and TNF-α converting enzyme (TACE). The standard pharmacological test procedures used, and results obtained which establish this biological profile are shown below.

Test Procedures for Measuring MMP-1, MMP-9, and MMP-13 Inhibition

These standard pharmacological test procedures are based on the cleavage of a thiopeptide substrates such as Ac-Pro-Leu-Gly(2-mercapto-4-methyl-pentanoyl)-Leu-Gly-OEt by the matrix metalloproteinases MMP-1, MMP-13 (collagenases) or MMP-9 (gelatinase), which results in the release of a substrate product that reacts calorimetrically with DTNB (5,5'-dithiobis(2-nitro-benzoic acid)). The enzyme activity is measured by the rate of the color increase. The thiopeptide substrate is made up fresh as a 20 mM stock in 100% DMSO and the DTNB is dissolved in 100% DMSO as a 100 mM stock and stored in the dark at room temperature. Both the substrate and DTNB are diluted together to 1 mM with substrate buffer (50 mM HEPES pH 7.5, 5 mM $CaCl_2$) before use. The stock of enzyme is diluted with buffer (50 mM HEPES, pH 7.5, 5 mM $CaCl_2$, 0.02% Brij) to the desired final concentration. The buffer, enzyme, vehicle or inhibitor, and DTNB/substrate are added in this order to a 96 well plate (total reaction volume of 200 μl) and the increase in color is monitored spectrophotometrically for 5 minutes at 405 nm on a plate reader and the increase in color over time is plotted as a linear line.

Alternatively, a fluorescent peptide substrate is used. In this test procedure, the peptide substrate contains a fluorescent group and a quenching group. Upon cleavage of the substrate by an MMP, the fluorescence that is generated is quantitated on the fluorescence plate reader. The assay is run in HCBC assay buffer (50 mM HEPES, pH 7.0, 5 mM $Ca^{+2}$, 0.02% Brij, 0.5% Cysteine), with human recombinant MMP-1, MMP-9, or MMP-13. The substrate is dissolved in methanol and stored frozen in 1 mM aliquots. For the assay, substrate and enzymes are diluted in HCBC buffer to the desired concentrations. Compounds are added to the 96 well plate containing enzyme and the reaction is started by the addition of substrate. The reaction is read (excitation 340 nm, emission 444 nm) for 10 min. and the increase in fluorescence over time is plotted as a linear line.

For either the thiopeptide or fluorescent peptide test procedures, the slope of the line is calculated and represents the reaction rate. The linearity of the reaction rate is confirmed ($r^2>0.85$). The mean (x±sem) of the control rate is calculated and compared for statistical significance (p<0.05) with drug-treated rates using Dunnett's multiple comparison test. Dose-response relationships can be generated using multiple doses of drug and $IC_{50}$ values with 95% Cl are estimated using linear regression.

Test Procedure for Measuring TACE Inhibition

Using 96-well black microtiter plates, each well receives a solution composed of 10 μL TACE (final concentration 1 μg/mL), 70 μL Tris buffer, pH 7.4 containing 10% glycerol (final concentration 10 mM), and 10 μL of test compound solution in DMSO (final concentration 1 μM, DMSO concentration <1%) and incubated for 10 minutes at room temperature. The reaction is initiated by addition of a fluorescent peptidyl substrate (final concentration 100 μM) to each well and then shaking on a shaker for 5 sec.

The reaction is read (excitation 340 nm, emission 420 nm) for 10 min. and the increase in fluorescence over time is plotted as a linear line. The slope of the line is calculated and represents the reaction rate.

The linearity of the reaction rate is confirmed ($r^2>0.85$). The mean (x±sem) of the control rate is calculated and compared for statistical significance (p<0.05) with drug-treated rates using Dunnett's multiple comparison test. Dose-response relationships can be generate using multiple doses of drug and $IC_{50}$ values with 95% Cl are estimated using linear regression.

Results of the above in vitro matrix metalloproteinase inhibition and TACE inhibition following these standard pharmacological test procedures are given in Table 1 below.

TABLE 1

| Ex. No. | IC50 (nM) | | | |
| --- | --- | --- | --- | --- |
| | MMP-1 | MMP-9 | MMP-13 | TACE |
| 13 | 2668 | 36 | 21 | 51 |
| 16 | 138 | 3 | 3 | 36 |
| 19 | 8806 | 21 | 25 | 62 |
| 22 | 877 | 4 | 6 | 48 |
| 26 | 50 | — | 4 | 116 |
| 45 | 2353 | 9 | 7 | 71 |
| 46 | 675 | — | 4 | 515 |
| 47 | 32% (1 μM) | — | 5 | 1400 |

The present invention will now be illustrated with reference to the following, non-limiting examples.

EXAMPLE 1

4-But-2-ynyloxybenzenesulfonyl fluoride

To a solution of 1-dimethyl-2-aminopropyne (10 g, 120 mmol) in tetrahydrofuran (270 ml) at −78° C. was added n-butyllithium (52.8 mL, 132 mmol) and the resulting mixture was stirred for 20 minutes. A suspension of formaldehyde (3.96 g, 132 mmol) in tetrahydrofuran (150 ml) was then added and the mixture was stirred at −78° C. for 1 hour. The reaction was allowed to warm to room temperature, quenched with a saturated ammonium chloride solution and extracted with ethyl acetate. The removal of the solvent in vacuo gave 10 g (74%) of the product.

$^1$H NMR (300 MHz, CDCl$_3$): δ 2.30 (s, 6H), 3.26 (m, 2H), 4.26 (m, 2H).

EXAMPLE 2

1-(tert-Butyl) 4-methyl 1,4-piperidinecarboxylate

To a solution of product from Example 1 (8 g, 70.8 mmol) in acetone (300 ml) was added methyl iodide (15 g, 105.6 mmol) and the resulting mixture was stirred for 4 hours at room temperature. The solid was collected and dried to give 13.5 g (75%) of the salt.

EXAMPLE 3

Buta-2,3-diene-1-ol

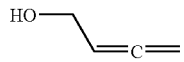

To a suspension of product from Example 2 (10 g, 39.2 mmol) in tetrahydrofuran (200 ml) was added lithium aluminium hydride (2.23 g, 58.7 mmol) and the resulting mixture was stirred for 4 hours. The mixture was quenched with Rochelle's salt and extracted with diethyl ether. The organic layer was washed with 1N hydrochloric acid, saturated sodium thiosulfate solution, saturated sodium chloride and dried over anhydrous sodium sulfate. The solvent was removed in vacuo to give 2.15 g (98%) of the product as an oil.

$^1$H NMR(300 MHz, CDCl$_3$): δ 1.73 (m, 1H), 4.15 (m, 2H), 4.86 (m, 2H), 5.36 (m, 1H); $^{13}$C NMR(75 MHz, CDCl$_3$): δ 60.6, 77.5, 91.2, 208.0.

EXAMPLE 4

1-(tert-Butoxycarbonyl)-4-{[4-(2-butynyloxy)phenyl]sulfonyl}-4-piperidinecarboxyic acid

A solution of thionyl chloride (16 ml, 200 mmol) and dimethylformamide (0.3 ml) was quickly added to solid sodium 4-hydroxybenzenesulfonate (10 g, 40 mmol) in a flask and the resulting mixture was heated at 60° C. for 3 hours. The mixture was poured into ice with vigorous stirring, methylene chloride was added and aqueous layer was separated. The aqueous layer was extracted with additional methylene chloride and the organic layers were washed with ice-water and dried over anhydrous sodium sulfate. The solvent was removed in vacuo to give 4 g (52%) of the product as a solid.

$^1$H NMR(300 MHz, DMSO-d$_6$): δ 5.36 (brs, 1H), 6.98 (d, 2H, J=9.0 Hz), 7.96 (d, 2H, J=9.0 Hz).

EXAMPLE 5

4-(2,3-Butadienyloxy)benzenesulfonyl chloride

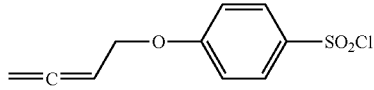

To a solution of product from Example 4 (1.98 g, 10.28 mmol) in benzene (70 ml) was added product from Example 3 (600 mg, 8.57 mmol) followed by diethylazodicarboxylate (1.6 ml, 10.28 mmol). A solution of triphenylphosphine (2.7 g, 10.28 mmol) in benzene (10 ml) was added, dropwise, to the reaction mixture and the resulting solution was stirred for 15 minutes at room temperature. The solid formed was collected and removal of the solvent in vauo gave the crude product, which was purified by flash chromatography to give 850 mg (41%) of the product.

IR: 1956, 1590, 1576, 1372, 1260, 1166, 832 cm$^1$; $^1$H NMR(300 MHz, CDCl$_3$): δ 4.68 (m, 2H), 4.93 (m, 2H), 5.38 (m, 1H), 7.04 (d, 2H, J=9.0 Hz), 7.98 (d, 2H, J=9.0 Hz); $^{13}$C NMR(75 MHz, CDCl$_3$): δ 66.9, 77.6, 86.3, 115.8, 129.8, 136.5, 164.0, 210.0.

EXAMPLE 6

4-(Methoxy)penta-2-ynyl-1-ol

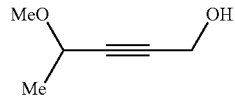

To a solution of n-butyllithium (64 ml, 156.8 mmol) in tetrahydrofuran (300 ml) at −78° C. was added a solution of tetrahydro-2-(2-propynyloxy)-2H-pyran (20 g, 142.6 mmol) in tetrahydrofuran (100 ml), dropwise, and the mixture was stirred for 10 minutes. A solution of acetaldehyde (8 ml, 142.6 mmol) was then added and the resulting mixture was stirred for 20 minutes at −78° C. Neat methyl iodide (36 ml, 570 mmol) was added and the mixture was allowed to warm to room temperature. Hexamethyldiphosphorylamide (40 ml) was added while the reaction was warming to room temperature and the mixture was stirred for 1.5 hours. The reaction was quenched with water and extracted with diethyl ether. To a solution of the crude product in methanol (200 ml) was added pyridinium p-toluenesulfonate (1.5 g). The mixture was stirred overnight, neutralized with a saturated sodium bicarbonate solution, and the solventl was removed in vacuo. The crude product was partitioned between water and ethyl acetate. The organic layer was dried over anhydrous sodium sulfate and the residue was distilled (95° C. at 20 mmHg) to give 12 g (75%) of the product as a liquid.

IR: 3416, 2936, 1449, 1112, 850 cm$^{−1}$; $^1$H NMR(300 MHz, CDCl$_3$): δ 1.43 (d, 3H, J=6.6 Hz), 1.79 (brs, 1H), 3.40

(s, 3H), 4.11 (m, 1H), 4.32 (m, 2H); $^{13}$C NMR(75 MHz, CDCl$_3$): δ 22.2, 51.4, 56.7, 67.2, 83.6, 85.7; MS(ES): m/z 115 (M+H)$^+$.

EXAMPLE 7

Penta-2,3-dien-1-ol

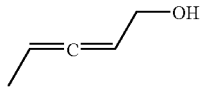

To a solution of product from Example 6 (430 mg, 3.77 mmol) in diethyl ether (30 ml) was added, in portions, lithium aluminum hydride (287 mg, 7.54 mmol) at room temperature and the mixture was stirred for 10 minutes. Solid iodine was added in one batch to the cooled (−78° C.) solution and the resulting mixture was stirred for 2 hours. The −78° C. bath was replaced with an ice-bath and a saturated solution of Rochelle's salt was added, dropwise, until distinct layers are formed. The excess iodine was removed by addition of a sodium thiosulfate solution. The diethyl ether layer was separated, dried over anhydrous sodium sulfate and removal of the solvent in vacuo gave 350 mg (91%) of the product.

IR: 3379, 2936, 1967, 1725, 1374, 1080, 877 cm$^{-1}$; $^1$H NMR(300 MHz, CDCl$_3$): δ 1.69 (m, 3H), 2.27 (brs, 1H), 4.14 (m, 2H), 5.26 (m,2H); $^{13}$C NMR(75 MHz, CDCl$_3$): δ 14.5, 61.0, 88.6, 91.4, 205.0.

EXAMPLE 8

1-Chloro-penta-2,3-diene

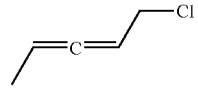

To a solution of triphenylphosphene (1.36 g, 5.2 mmol) in methylene chloride (25 ml) was added, in portions, triphenylphosgene (593 mg, 2.0 mmol) and the resulting mixture was stirred for 5 minutes at room temperature. A solution of product from Example 7 (400 mg, 4.76 mmol) was added and the mixture was stirred for 30 minutes.

The reaction mixture was distilled in vacuo, collection the distillate in a −78° C. trap. The distillate was redistilled (b.p. 56° C. at 100 mmHg) to give 200 mg (41%) of the product as a liquid.

$^1$H NMR(300 MHz, CDCl$_3$): δ 1.69 (m, 3H), 4.05 (m, 2H), 5.27 (m, 2H).

EXAMPLE 9

4-(2,3-Pentadienyloxy)benzenesulfonic acid sodium salt

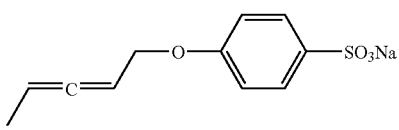

To a suspension of sodium 4-hydroxybenzenesulfonate (1.3 g, 5.6 mmol) in iso-propanol (20 ml) was added product from Example 8 (700 mg, 6.8 mmol) followed by 1N sodium hydroxide (6.1 ml, 6.1 mmol) and the resulting mixture was heated at 65-70° C. for 15 hours. The reaction mixture was concentrated in vacuo, the solid collected and washed with diethy ether to give 880 mg (53%) of the product as a solid.

IR: 1973, 1182, 1139, 1051, 834 cm$^{-1}$; $^1$H NMR(300 MHz, D$_2$O): δ 1.46 (m, 3H), 4.53 (m, 2H), 5.22 (m, 2H), 6.95 (d 2H, J=9.0 Hz), 7.64 (d, 2H, J=9.0 Hz); $^{13}$C NMR(75 MHz, D$_2$O): δ 13.3, 66.5, 86.5, 88.9, 115.6, 127.9, 135.5, 160.1, 206.1; HR-MS: m/z Calculated for C$_{11}$H$_{12}$O$_4$S(M−H): 239.0383; Found 239.0386.

EXAMPLE 10

4-(2,3-Pentadienyloxy)benzenesulfonyl chloride

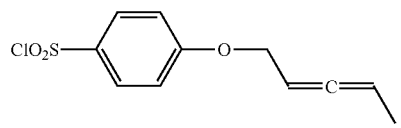

To a suspension of product from Example 9 (740 mg, 2.48 mmol) in acetonitrile (2 ml) and sulfolane (2 ml) was added phosphoryl chloride (0.9 ml, 9.93 mmol) and the resulting mixture was heated at 60-65° C. for 2 hours. The mixture was cooled in ice and cold water was added, dropwise, while stirring was continued for an additional 15 minutes. The reaction mixture was extracted with ethyl acetate and the organic layer was dried over anhydrous sodium sulfate. The crude residue was purified by flash chomatography to give 415 mg (65%) of the product.

IR: 2928, 1970, 1590, 1576, 1166, 1085, 833 cm$^{-1}$; $^1$H NMR(300 MHz, CDCl$_3$): δ 1.74 (m, 3H), 4.66 (m, 2H), 5.29 (m, 2H), 7.06 (d, 2H, J=9.0 Hz), 7.99 (d, 2H, J=9.0 Hz); $^{13}$C NMR(75 MHz, CDCl$_3$): δ14.1, 67.4, 86.2, 88.7, 115.9, 129.8, 136.4, 164.1, 208.0; MS-ES:m/z 258(M+H)$^+$.

EXAMPLE 11

Methyl 2-({[4-(2,3-butadienyloxy)phenyl]sulfonyl}amino)-3-methylbutanoate

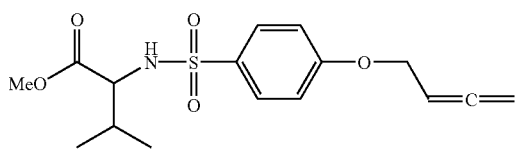

To a solution of DL-valine methyl ester hydrochloride (527 mg, 3.15 mmol) was added triethylamine (579 mg, 5.72 mmol) followed by product from Example 5 (700 mg, 2.86 mmol) and the resulting mixture was stirred for 10 hours at room temperature. The solvent was removed in vacuo and the residue was partitioned between water and ethyl acetate. The organic layer was washed with 1N hydrochloric acid, saturated sodium bicarbonate, saturated sodium chloride and dried over anhydrous sodium sulfate. Removal of the solvent in vacuo gave 850 mg (87%) of the product as a solid.

IR: 3283, 2969, 1962, 1737, 1595, 1259, 839 cm$^{-1}$; $^1$H NMR(300 MHz, CDCl$_3$): δ 0.87 (d, 3H, J=6.9 Hz), 0.95 (d, 3H, J=6.9 Hz), 202 (m, 2H), 3.47 (s, 3H), 3.71 (m, 1H), 4.62 (m, 2H), 4.90 (m, 2H), 5.02 (d, 1H, J=10.2 Hz), 5.36 (m, 1H), 6.96 (d, 2H, J=9.0 Hz), 7.75 (d, 2H, J=9.0 Hz); $^{13}$C

NMR(75 MHz, CDCl$_3$): δ 17.4, 18.9, 31.6, 52.2, 61.0, 66.1, 77.2, 86.3, 115.0, 129.4, 131.4, 161.8, 171.9, 209.7; HR-MS: m/z Calculated for C$_{16}$H$_{21}$NO$_5$S: 340.1213; Found 340.1221.

EXAMPLE 12

N-{[4-(2,3-Butadienyloxy)phenyl]sulfonyl}valine

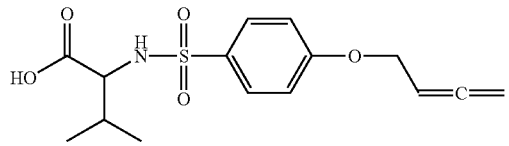

To a solution of product from Example 11 (300 mg, 0.88 mmol) in a mixture of tetrahydrofuran (5 ml), methanol (5 ml), and water (3 ml) was added lithium hydroxide (64 mg, 2.67 mmol) and the resulting mixture was heated at 60° C. for 8 hours. The mixture was concentrated in vacuo followed by the addition of water.

The solution was acidified to pH ~2 with 1N hydrochloric acid and extracted with ethyl acetate. The organic layer was washed with saturated sodium chloride, dried over anhydrous sodium sulfate, and the solvent was removed to give 250 mg (81%) of the product.

IR: 3266, 2967, 1961, 1723, 1594, 1332, 1163, 829 cm$^{-1}$; $^1$H NMR(300 MHz, DMSO-d$_6$): δ 0.78 (d, 3H, J=6.3 Hz), 0.81 (d, 3H, J=6.3 Hz), 1.92 (m, 1H), 3.31 (s, 3H), 3.44 (m, 1H), 4.63 (m, 2H), 4.98 (m, 2H), 5.51 (m, 1H), 7.06 (d, 2H, J=9.0 Hz), 7.69 (d, 2H, J=9.0 Hz), 7.82 (d, 1H, J=9.3 Hz), 12.51 (s, 1H); $^{13}$C NMR(75 MHz, DMSO-d$_6$): δ 17.7, 18.9, 30.2, 61.0, 65.3, 77.0, 86.3, 114.6, 128.6, 133.0, 160.6, 172.1, 208.7; HR-MS: m/z Calculated for C$_{15}$H$_{19}$NO$_5$S: 326.1057; Found 326.1052.

EXAMPLE 13

2-({[4-(2,3-Butadienyloxy)phenyl]sulfonyl}amino)-N-hydroxy-3-methylbutanamide

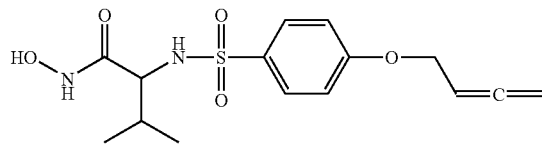

To a solution of product from Example 12 (210 mg, 0.65 mmol) in dimethylformamide (6 ml) was added 1-hydroxybenzotriazol (105 mg, 0.78 mmol), 1-[3-(dimethylamino)propyl]-3-ethylcarbodimide hydrochloride (173 mg, 0.90 mmol), and N-methylmorpholine (0.106 mmol, 0.97 mmol) and the resulting mixture was stirred for 1 hour at room temperature. A 50% aqueous solution of hydroxylamine (0.119 ml, 1.94 mmol) was added and the mixture was stirred for 15 hours at room temperature. The reaction mixture was concentrated in vacuo, diluted with water, and extracted with ethyl acetate. The organic layer was washed with 1N hydrochloric acid, water, saturated sodium bicarbonate, saturated sodium chloride and dried over anhydrous sodium sulfate. Removal of the solvent in vacuo gave 100 mg (45%) of the product.

IR: 3313, 2973, 1954, 1671, 1594, 1324, 1253, 1153, 829 cm$^{-1}$; $^1$H NMR(300 MHz, DMSO-d$_6$): δ 0.72 (t, 6H, J=7.2 Hz), 1.75 (m, 1H), 3.25 (m, 1H), 4.64 (m, 2H), 4.98 (m, 2H), 5.51 (m, 1H), 7.06 (d, 2H, J=9.0 Hz), 7.67 (d, 2H, J=90 Hz), 7.75 (d, 1H, J=9.3 Hz), 8.78 (d, 1H, J=1.8 Hz), 10.48 9d, 1H, J=1.8 Hz); $^{13}$C NMR(75 MHz, DMSO-d$_6$): δ 18.8, 19.2, 31.0, 59.9, 65.7, 77.5, 84.2, 86.8, 115.0, 128.8, 133.8, 160.9, 167.1, 209.2; HR-MS: m/z Calculated for C$_{15}$H$_{20}$N$_2$O$_5$S: 341.1166; Found 341.1163.

EXAMPLE 14

Methyl 2-[{[4-(2,3-butadienyloxy)phenyl]sulfonyl}(methyl)amino]-3-methylbutanoate

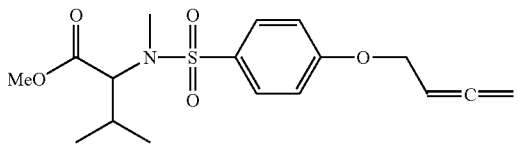

A solution of product from Example 11 (400 mg, 1.18 mmol) in tetrahydrofuran (10 ml) was added to a suspension of 60% sodium hydride (57 mg, 1.42 mmol) in tetrahydrofuran (2 ml) and the resulting mixture was stirred for 30 minutes, at which time methyl iodide (335 mg, 2.36 mmol) was added. The resulting mixture was stirred for 15 hours and partitioned between ethyl acetate and water. The organic layer was washed with saturated sodium chloride, dried over anhydrous sodium sulfate and the crude residue was purified by flash chromatography to give 350 mg (84%) of the product.

IR: 2971, 1958, 1735, 1593, 13336, 1255, 1144, 993 cm$^{-1}$; $^1$H NMR(300 MHz, CDCl$_3$): δ 0.92 (d, 3H, J=6.6 Hz), 0.98 (d, 3H, J=6.6 Hz), 2.07 (m, 1H), 2.86 (s, 3H), 3.43 (s, 3H), 4.11 (d, 1H, J=10.8 Hz), 4.62 (m, 2H), 4.89 (m, 2H), 5.37 (m, 1H), 6.96 (d, 2H, J=9.0 Hz), 7.72 (d, 2H, J=9.0 Hz); $^{13}$C NMR(75 MHz, CDCl$_3$): δ 19.1, 27.8, 29.9, 51.3, 64.6, 66.1, 77.2, 86.3, 114.7, 129.4, 130.9, 161.5, 170.7, 209.7; HR-MS: m/z Calculated for C$_{17}$H$_{23}$NO$_5$S: 354.1370; Found 354.1378.

EXAMPLE 15

N-{[4-(2,3-Butadienyloxy)phenyl]sulfonyl}valine

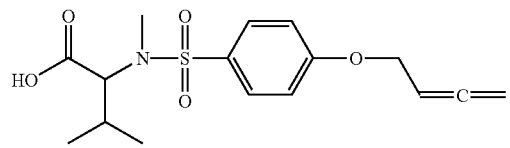

The procedure of Example 12 was followed using the product from Example 14 (300 mg, 0.85 mmol) and lithium hydroxide (41 mg, 1.7 mmol) in tetrahydrofuran (3 ml), methanol (3 ml), and water (1.5 ml) to give 247 mg (86%) of the product.

IR: 2970, 1956, 1707, 1592, 1334, 1154, 835 cm$^{-1}$; $^1$H NMR(300 MHz, DMSO-d$_6$): δ 0.82 (d, 3H, J=6.6 Hz), 0.89 (d, 3H, J=6.6 Hz), 1.95 (m, 1H), 2.76 (s, 3H), 3.88 (d, 1H, J=10.5 Hz), 4.64 (m, 2H), 5.00 (m, 2H), 5.51 (m, 1H), 7.08

(d, 2H, J=9.0 Hz), 7.69 (d, 2H, J=9.0 Hz); HR-MS: m/z Calculated for $C_{16}H_{21}NO_5S$: 340.1213; Found 340.1204.

EXAMPLE 16

2-[{[4-(2,3-Butadienyloxy)phenyl]sulfonyl}(methyl)amino]-N-hydroxy-3-methylbutanamide

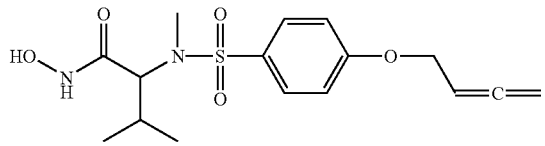

The procedure of Example 13 was followed using the product from Example 15 (250 mg, 0.74 mmol), 1-hydroxybenzotriazol (119 mg, 0.88 mmol), 1-[3-(dimethylamino)-propyl]-3-ethylcarbodimide hydrochloride (199 mg, 1.04 mmol), N-methylmorpholine (0.122 mmol, 1.11 mmol), and hydroxylamine (0.226 ml, 3.7 mmol) to give 150 mg (57%) of the product.

IR: 3351, 3238, 2969, 1957, 1653, 1594, 1327, 1150, 834 cm$^{-1}$; $^1$H NMR(300 MHz, DMSO-d$_6$): δ 0.78 (m, 6H), 2.02 (m, 1H), 2.80 (s, 3H), 3.70 (d, 1H, J=10.8 Hz), 4.65 (m, 2H), 5.00 (m, 2H), 5.51 (m, 1H), 7.08 (d, 2H, J=9.0 Hz), 7.69 (d, 2H, J=9.0 Hz), 8.87 (s, 1H), 10.80 (s, 1H); $^{13}$C NMR(75 MHz, DMSO-d$_6$): δ 19.1, 19.5, 27.1, 30.0, 62.0, 65.8, 77.5, 86.7, 115.3, 129.3, 131.3, 161.3, 165.7, 209.2; HR-MS: m/z Calculated for $C_{16}H_{22}N_2O_5S$: 355.1322; Found 355.1313.

EXAMPLE 17

Methyl 3-methyl-2-({[4-(2,3-pentadienyloxy)phenyl]sulfonyl}amino)butanoate

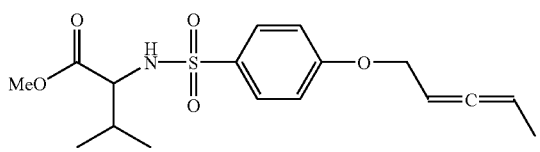

The procedure of Example 11 was followed using DL-valine methyl ester hydrochloride (246 mg, 1.47 mmol), the product from Example 10 (388.0 mg, 1.5 mmol), and triethylamine (297 mg, 2.94 mmol) in methylene chloride (10 ml) to give 350 mg (68%) of the product.

IR: 3261, 2967, 1968, 1732, 1595, 1159, 996, 834 cm$^{-1}$; $^1$H NMR(300 MHz, CDCl$_3$): δ 0.87 (d, 3H, J=6.9 Hz), 0.94 (d, 3H, J=6.9 Hz), 1.67 (m, 3H), 2.02 (m, 1H), 3.46 (s, 3H), 3.71 (m, 1H), 4.59 (m, 2H), 5.26 (m, 3H), 6.97 (d, 2H, J=9.0 Hz), 7.77 (d, 2H, J=9.0 Hz); $^{13}$C NMR(75 MHz, CDCl$_3$): δ 13.7, 17.5, 18.9, 31.5, 52.2, 61.0, 66.7, 86.2, 88.0, 114.9, 129.3, 131.2, 161.8, 171.8, 206.0; HR-MS: m/z Calculated for $C_{17}H_{23}NO_5S$: 353.1298; Found 353.1297.

EXAMPLE 18

N-{[4-(2,3-Pentadienyloxy)phenyl]sulfonyl}valine

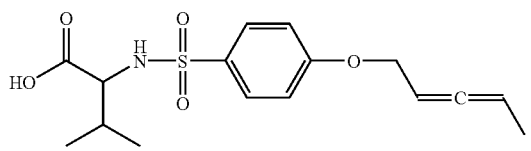

The procedure of Example 12 was followed using the product from Example 17 (320 mg, 0.91 mmol) and lithium hydroxide (64 mg, 2.67 mmol) in tetrahydrofuran (5 ml), methanol (5 ml), and water (3 ml) to give 250 mg (81%) of the product.

IR: 3279, 2969, 1972, 1715, 1595, 1160, 835 cm$^{-1}$; $^1$H NMR(300 MHz, acetone-d$_6$): δ 0.89 (d, 3H, J=6.9 Hz), 0.95 (d, 3H, J=6.9 Hz 1.63 (m, 3H), 2.09 (m, 1H), 3.14 (brs, 1H), 3.68 (m, 1H), 4.65 (m, 2H), 5.32 (m, 2H), 6.43 (d, 1H, J=9.2 Hz), 7.05 (d, 2H, J=9.0 Hz), 7.78 (d, 2H, J=9.0 Hz); $^{13}$C NMR(75 MHz, acetone-d$_6$): δ 14.3, 18.2, 19.8, 32.3, 62.2, 67.5, 87.8, 88.7, 116.0, 130.4, 134.3, 162.8, 173.0, 206.0; HR-MS: m/z Calculated for $C_{16}H_{21}NO_5S$: 339.1141; Found 339.1116.

EXAMPLE 19

N-Hydroxy-3-methyl-2-({[4-(2,3-pentadienyloxy)phenyl]sulfonyl}amino)butanamide

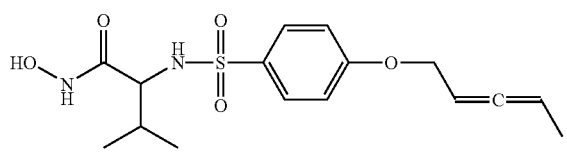

The procedure of Example 13 was followed using the product from Example 18 (230 mg, 0.67 mmol), 1-hydroxybenzotriazol (80 mg, 0.59 mmol), 1-[3-(dimethylamino)-propyl]-3-ethylcarbodimide hydrochloride (132 mg, 0.69 mmol), N-methylmorpholine (0.81 mmol, 0.74 mmol), and hydroxylamine (0.150 ml, 2.45 mmol) in dimethylformamide (5 ml) to give 100 mg (42%) of the product.

IR: 3739, 3318, 2969, 1971, 1672, 1595, 1323, 1154, 998 cm$^{-1}$; $^1$H NMR(300 MHz, DMSO-d$_6$): δ 0.72 (m, 6H), 1.59 (m, 3H), 1.75 (m, 1H), 3.24 (t,1H, J=8.4 Hz), 4.60 (dd, 2H, J$_1$=2.4 Hz, J$_2$=6.3 Hz), 5.35 (m, 2H), 7.05 (d, 2H, J=9.0 Hz), 7.68 (d, 2H, J=9.0 Hz), 7.70 (m, 1H), 8.77 (s, 1H), 10.47 (s, 1H); $^{13}$C NMR(75 MHz, DMSO-d$_6$): δ 13.4, 18.4, 18.8, 30.6, 59.5, 65.7, 86.6, 87.3, 114.6, 128.3, 133.3, 160.5, 166.7, 205.3. HR-MS: m/z Calculated for $C_{16}H_{22}N_2O_5S$ (M+Na): 377.1141; Found 377.1141.

EXAMPLE 20

Methyl 3-methyl-2-(methyl{[4-(2,3-pentadienyloxy)phenyl]sulfonyl}amino)butanoate

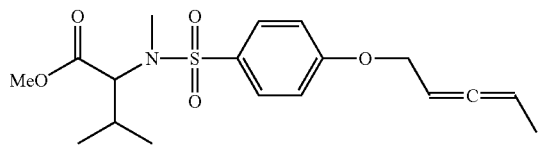

The procedure of Example 14 was followed using the product from Example 17 (300 mg, 0.85 mmol), sodium hydride (41 mg, 1.02 mmol), and methyl iodide (241 mg, 1.7 mmol) in tetrahydrofuran (8 ml) to give 240 mg (77%) of the product.

IR: 2965, 1969, 1739, 1594, 1496, 1340, 1148, 834 cm$^1$; $^1$H NMR(300 MHz, CDCl$_3$): δ 0.92 (d, 3H, J=6.6 Hz), 0.99

(d, 3H, J=6.6 Hz), 1.68 (m, 3H), 2.08 (m, 1H), 2.85 (s, 3H), 3.43 (s, 3H), 4.13 (d, 1H, J=6.9 Hz), 4.58 (m, 2H), 5.27 (m, 1H), 6.96 (d, 2H, J=9.0 Hz), 7.71 (d, 2H, J=9.0 Hz); $^{13}$C NMR(75 MHz, CDCl$_3$): δ 13.7, 19.1, 19.2, 27.8, 29.9, 51.3, 64.6, 66.7, 67.3, 77.2, 86.3, 88.0, 114.8, 129.4, 130.7, 161.6, 170.7, 206.3; HR-MS: m/z Calculated for C$_{18}$H$_{25}$NO$_5$S: 368.1526; Found 368.1533.

EXAMPLE 21

N-Methyl-N-{[4-(2,3-pentadienyloxy)phenyl]sulfonyl}valine

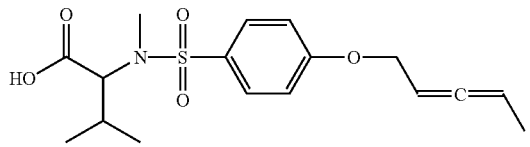

The procedure of Example 12 was followed using the product from Example 20 (240 mg, 0.65 mmol), and lithium hydroxide (31 mg, 1.31 mmol) in tetrahydrofuran (2 ml), methanol (2 ml), and water (1 ml) to give 200 mg (87%) of the product.

IR: 3245, 2967, 1970, 1714, 1594, 1151, 833 cm$^{-1}$; $^1$H NMR(300 MHz, DMSO-d$_6$): δ 0.82 (d, 3H, J=6.6 Hz), 0.89 (d, 3H, J=6.6 Hz), 1.59 (m, 3H), 2.75 (s, 3H), 3.88 (d, 1H, J=10.5 Hz), 4.62 (m, 2H), 5.38 (m, 2H), 7.08 (d, 2H, J=9.0 Hz), 7.68 (d, 2H, J=9.0 Hz), 12.80 (brs, 1H); $^{13}$C NMR(75 MHz, DMSO-d$_6$): δ 13.4, 18.9, 19.1, 27.0, 29.5, 64.4, 65.8, 86.5, 87.4, 114.9, 129.0, 130.4, 144.7, 161.0, 171.1, 205.4; HR-MS: m/z Calculated for C$_{17}$H$_{23}$NO$_5$S: 354.1370; Found 354.1364.

EXAMPLE 22

N-Hydroxy-3-methyl-2-(methyl{[4-(2,3-pentadienyloxy)phenyl]sulfonyl}amino)butanamide

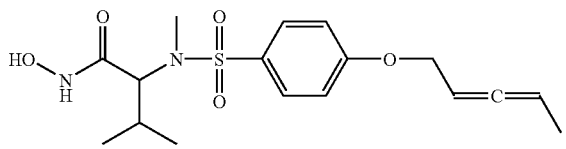

The procedure of Example 13 was followed using the product from Example 21 (185 mg, 0.52 mmol), 1-hydroxybenzotriazol (84 mg, 0.62 mmol), 1-[3-(dimethylamino)propyl]-3-ethylcarbodimide hydrochloride (140 mg, 0.73 mmol), N-methylmorpholine (0.86 mmol, 0.78 mmol), and hydroxylamine (0.159 ml, 2.6 mmol) in dimethylformamide (5 ml) to give 120 mg (63%) of the product.

IR: 3357, 3223, 2918, 1970, 1653, 1596, 1327, 1150, 998 cm$^{-1}$; $^1$H NMR(300 MHz, DMSO-d$_6$): δ 0.78 (m, 6H), 1.60 (m, 3H), 2.02 (m, 1H), 2.79 (s, 3H), 3.71 (d, 1H, J=10.8 Hz), 4.62 (m, 2H), 5.38 (m, 1H), 7.06 (d, 2H, J=8.7 Hz), 7.69 (d, 2H, J=8.7 Hz), 8.86 (s, 1H), 10.78 (s, 1H); $^{13}$C NMR(75 MHz, DMSO-d$_6$): δ 13.4, 18.6, 19.1, 26.6, 29.5, 61.6, 65.8, 86.6, 87.4, 114.9, 128.8, 130.8, 160.9, 165.3, 205.4; HR-MS: m/z Calculated for C$_{17}$H$_{24}$N$_2$O$_5$S: 369.1479; Found 369.1469.

EXAMPLE 23

Methyl (3S)-2,2-dimethyl-3-thiomorpholinecarboxylate

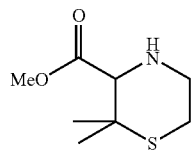

To a solution of 1,2-dibromoethane (6.77 g, 36 mmol) in dimethylformamide (25 ml) was added, over a period of 30 minutes, a solution of D-penicillamine methyl ester hydrochloride (6 g, 30 mmol) and 1,8-diazobicyclo[5.4.0]undeca-7-ene (13.7 g, 90 mmol) in dimethylformamide (50 ml). The resulting mixture was stirred for 18 hours at room temperature. The reaction mixture was poured into a saturated sodium bicarbonate solution and extracted with ethyl acetate. The organic layer was dried over anhydrous sodium sulfate and the solvent was removed in vacuo to give 5.5 g (97%) of the product.

$^1$H NMR(300 MHz, CDCl$_3$): δ 1.29 (s, 3H), 1.42 (s, 3H), 1.78 (s, 1H), 2.29 (m, 1H), 2.94 (m, 3H), 3.39 (m, 1H), 3.72 (s, 3H).

EXAMPLE 24

Methyl (3S)-4-{[4-(2,3-butadienyloxy)phenyl]sulfonyl}-2,2-dimethyl-3-thiomorpholinecarboxylate

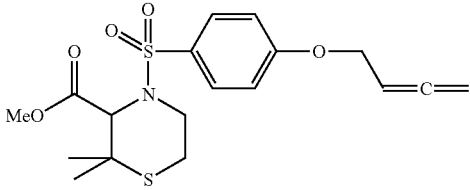

To a solution of product from Example 23 (155 mg, 0.82 mmol) in methylene chloride (5 ml) was added N-methylmorpholine (0.180 ml, 1.64 mmol) followed by the product from Example 5 (200 mg, 0.82 mmol). The resulting mixture was stirred for 15 hours at room temperature. The solvent was removed in vacuo and the residue dissolved in ethyl acetate. The organic layer was washed with 1N hydrochloric acid, saturated sodium bicarbonate, saturated sodium chloride and dried over anhydrous sodium sulfate. The crude residue was purified by flash chromatography to give 170 mg (52%) of the product.

IR: 2960, 1957, 1745, 1594, 1495, 1156, 877 cm$^1$; $^1$H NMR(300 MHz, CDCl$_3$): δ 1.26 (s, 3H), 1.61 (s, 3H), 2.46 (m, 1H), 3.12 (m, 1H), 3.41 (s, 3H), 3.76 (m, 1H), 4.05 (m, 1H), 4.41 (s, 1H), 4.62 (m, 2H), 4.89 (m, 2H), 5.36 (m, 1H), 6.94 (d, 2H, J=9.0 Hz), 7.65 (d, 2H, J=9.0 Hz); $^{13}$C NMR(75 MHz, CDCl$_3$): δ 24.6, 27.2, 28.4, 29.7, 40.1, 41.2, 51.3, 62.7, 66.1, 86.3, 114.9, 129.1, 130.7, 161.7, 168.7, 209.6; HR-MS: m/z Calculated for C$_{18}$H$_{23}$NO$_5$S$_2$: 398.1090; Found 398.1089.

EXAMPLE 25

(3S)-4-{[(4-(2,3-Butadienyloxy)phenyl]sulfonyl}-2,2-dimethyl-3-thiomorpholinecarboxylic acid

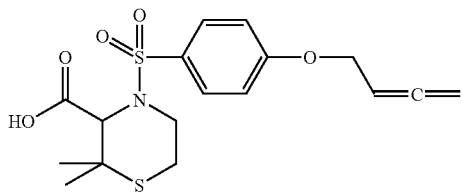

The procedure of Example 12 was followed using the product from Example 24 (150 mg, 0.38 mmol), lithium hydroxide (18 mg, 0.76 mmol) in tetrahydrofuran (2 ml), methanol (2 ml), and water (1 ml) to give 50 mg of product (53%, based on unreacted starting material).

$^1$H NMR(300 MHz, acetone-$d_6$): δ 1.35 (s, 3H), 1.55 (s, 3H), 2.52 (m, 1H), 3.05 (m, 1H), 3.82 (m, 1H), 4.02 (m, 1H), 4.40 (s, 1H), 4.68 (m, 2H), 4.94 (m, 2H), 5.46 (m, 1H), 7.07 (d, 2H, J=9.0 Hz), 7.75 (d, 2H, J=9.0 Hz); $^{13}$C NMR(75 MHz, acetone-$d_6$): δ 24.5, 27.3, 28.4, 40.0, 41.1, 62.7, 66.2, 77.2, 86.2, 115.0, 129.3, 130.7, 162.0, 172.3, 209.6; HR-MS: m/z Calculated for $C_{17}H_{21}NO_5S_2$ 384.0933; Found 384.0932.

EXAMPLE 26

(3S)-4-{[4-(2,3-Butadienyloxy)phenyl]sulfonyl}-N-hydroxy-2,2-dimethyl-3-thiomorpholinecarboxamide

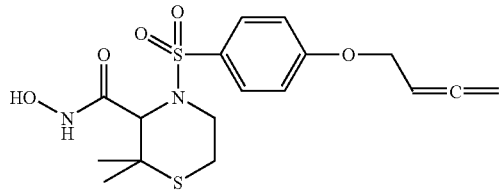

The procedure of Example 13 was followed using the product from Example 25 (65 mg, 0.17 mmol), 1-hydroxybenzotriazol (28 mg, 0.20 mmol), 1-[3-(dimethylamino)propyl]-3-ethylcarbodimide hydrochloride (46 mg, 0.24 mmol), N-methylmorpholine (0.028 ml, 0.26 mmol), and hydroxylamine (0.052 ml, 0.85 mmol) in dimethylformamide (1.5 ml) to give 40 mg (59%) of the product.

IR: 3351, 3241, 2963, 1960, 1655, 1594, 1153, 874 cm$^{-1}$; $^1$H NMR(300 MHz, DMSO-$d_6$): δ 1.22 (s, 3H), 1.46 (s, 3H), 2.61 (m, 1H), 2.93 (m, 1H), 3.80 (m, 1H), 4.02 (m, 1H), 4.09 (s, 1H), 4.72 (m, 2H), 5.07 (m, 2H), 5.58 (m, 1H), 7.13 (d, 2H, J=9.0 Hz), 7.68 (d, 2H, J=9.0 Hz), 8.91 (s, 1H), 10.8 (s, 1H); $^{13}$C NMR(75 MHz, DMSO-$d_6$): δ 24.0, 26.5, 28.5, 41.0, 58.6, 65.4, 77.2, 86.4, 115.1, 128.7, 130.9, 161.1, 164.0, 208.9; HR-MS: m/z Calculated for $C_{17}H_{22}N_2O_5S_2$ 399.1042; Found 399.1039.

EXAMPLE 27 tert-Butyl (3S)-2,2-dimethyl-4-{[4-(2,3-pentadienyloxy)phenyl]sulfonyl}-3-thiomorpholinecarboxylate

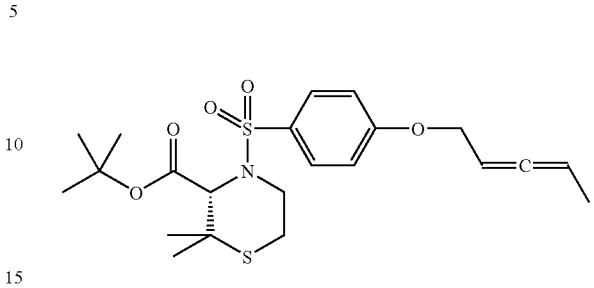

To a solution of tert-butyl 4-(4-hydroxybenzenesulfonyl)-2,2-dimethylthiomorpholine-3-carboxylate (697 mg, 1.8 mmol) in tetrahydrofuran (6 mL) was added triphenylphosphine (566 mg, 2.16 mmol) and the product from Example 7 (160 mg, 1.9 mmol) in tetrahydrofuran (4 mL) followed by diethylazodicarboxylate (0.312 mL, 1.98 mmol) at 0° C. The resulting mixture was stirred for 4 h at room temperature and the solvent was removed in vacuo. The residue was purified by silica gel column chromatagraphy to obtain the product (400 mg, 49%) as a white solid.

IR: 2975, 1969, 1736, 1594, 1154, 882 cm$^{-1}$; $^1$H NMR (400 MHz, CDCl$_3$): δ 1.30 (s, 9H), 1.32 (s, 3H), 1.61 (s, 3H), 1.68 (d, 3H, J=7.2 Hz), 2.43 (m, 1H), 3.12 (m, 1H), 3.87 (m, 1H), 4.04 (m, 1H), 4.32 (s, 1H) 4.57 (m, 1H), 5.27 (m, 1H), 5.26 (m, 1H), 6.94 (d, 2H, J=7.4 Hz), 7.66 (d, 2H, J=7.4 Hz); $^{13}$C NMR(100 MHz, CDCl$_3$): δ 13.7, 24.7, 27.6, 27.9, 28.7, 29.7, 40.3, 41.0, 63.1, 66.7, 82.1, 86.3, 88.0, 88.1, 115.1, 129.1, 131.5, 161.7, 167.6, 206.2, 206.3; HR-MS: m/z Calculated for $C_{22}H_{31}NO_5S_2$: 454.1716; Found 454.1713.

EXAMPLE 28

(3S)-2,2-dimethyl-4-{[4-(2,3-pentadienyloxy)phenyl]sulfonyl}-3-thiomorpholinecarboxylic acid

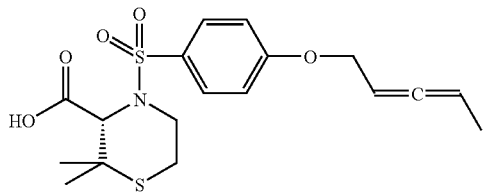

To a solution of the product from Example 27 (200 mg, 0.44 mmol) in methylene chloride (4 mL) was added trifluoroacetic acid (1 mL) and the resulting mixture was stirred for 2 h at room temperature. The solvents were removed in vacuo and the residue was purified by silica gel column chromatagraphy to obtain the product (120 mg, 69%) as a white solid.

$^1$H NMR(400 MHz, acetone-$d_6$): δ 1.35 (s, 3H), 1.55 (s, 3H), 1.63 (m, 3H), 2.5 (m, 1H), 3.05 (m, 1H), 3.80 (m, 1H), 4.01 (m, 1H), 4.39 (s, 1H), 4.65 (m, 1H), 5.33 (m, 1H), 7.07 (d, 2H, J=7.4 Hz), 7.71 (d, 2H, J=7.4 Hz); $^{13}$C NMR(100 MHz, acetone-$d_6$): δ 14.0, 15.6, 25.1, 27.9, 40.4, 41.9, 63.5, 66.1, 67.2, 87.4, 88.3, 115.8, 130.0, 162.7, 169.9, 206.1; HR-MS: m/z Calculated for $C_{18}H_{23}NO_5S_2$ 415.1355; Found 415.1349.

EXAMPLE 29

(3S)-N-Hydroxy-2,2-dimethyl-4-{[4-(2,3-pentadienyloxy)phenyl]sulfonyl}-3-thiomorpholinecarboxamide

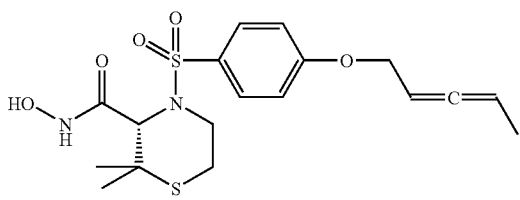

The procedure of Example 13 was followed using the product from Example 28 (190 mg, 0.46 mmol), 1-hydroxybenzotriazol (75 mg, 0.55 mmol), 1-[3-(dimethylamino)propyl]-3-ethylcarbodimide hydrochloride (123 mg, 0.64 mmol), N-methylmorpholine (0.076 ml, 0.69 mmol), and hydroxylamine (0.141 ml, 2.3 mmol) in dimethylformamide (4 ml) to give 50 mg (32%) of the product.

$^1$H NMR(400 MHz, DMSO-$d_6$): δ 1.16 (s, 3H), 1.39 (s, 3H), 1.60 (m, 3H), 2.54 (m, 1H), 2.86 (m, 1H), 3.74 (m, 1H), 3.95 (m, 1H), 4.03 (s, 1H), 4.63 (m, 1H), 5.35 (m, 1H), 7.06 (d, 2H, J=7.0 Hz), 7.62 (d, 2H, J=7.0 Hz), 8.82 (s, 1H), 10.80 (s, 1H). HR-MS: m/z Calculated for $C_{18}H_{24}N_2O_5S_2$: 413.1199; 413.1209.

EXAMPLE 30

Methyl 3-Hydroxy-2-(4-methoxybenzenesulfonylamino)propionate

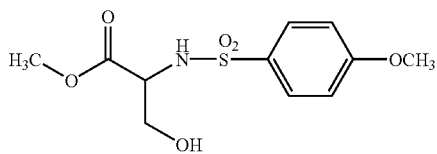

To a mixture of D,L-serine, methyl ester (5.0 g, 32.14 mmol) and triethylamine (15.7 ml, 0.012 mmol) in methylene chloride (100 ml), cooled to 0° C., was added, in portions, 4-methoxybenzenesulfonyl chloride (6.64 g, 32.14 mmol). The mixture was then stirred under argon at room temperature for 48 hours. The reaction was diluted with methylene chloride (100 ml), washed with water (60 ml), 2N citric acid (60 ml), saturated sodium chloride (60 ml), and dried over anhydrous sodium sulfate. The solvent was removed in vacuo to give a solid. Crystallization from ethyl acetate gave 5.0 g (54%) of the product as white crystals, mp 92-94° C.

Analysis. for $C_{11}H_{15}NO_6S$; Calc'd: C, 45.7; H, 5.2; N, 4.8; S, 11.1. Found: C, 45.6; H, 5.2; N, 4.8; S, 11.1. $^1$H NMR(300 MHz, CDCl$_3$): δ 2.04 (b, 1H), 3.63 (s, 3H), 3.87 (s, 3H,), 3.89 (d, 2H J=3.7 Hz), 3.97 (m, 1H), 5.66 (d, 1H, J=7.5 Hz); 6.98 (d, 2H, J=9 Hz); 7.8 (d, 2H, J=9 Hz); MS(ES):m/z 290.1 (M+H)$^+$.

EXAMPLE 31

Methyl 3-hydroxy-2-[(4-methoxybenzenesulfonyl)-(2-nitrobenzyl) amino]propionate

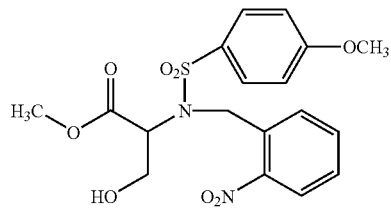

To a solution of methyl 3-hydroxy-2-(4-methoxybenzenesulfonylamino)-propionate (15.0 g 51.85 mmol) in N,N-dimethylformamide (125 ml), cooled in an ice bath, was added, portionwise, NaH (2.29 g 57.03 mmol, 60% in oil). The mixture was stirred at 0° C. for 20 minutes and then a solution of 2-nitrobenzyl bromide (12.32 g 57.03 mmol) in dry N,N-dimethylformamide (25 ml) was added, dropwise. The solution was stirred at room temperature for 48 hours and diluted with ethyl acetate (500 ml) and water. The organic layer was separated and the aqueous layer extracted with additional f ethyl acetate (250 ml). The combined organic layers were washed with water (200 ml), 1N sodium bicarbonate (200 ml), saturated sodium chloride (200 ml) and dried over sodium sulfate The solvent was removed in vacuo and the residual solid was triturated with ethyl acetate, cooled and filtered to give 13.5 g (61%) of white crystals, mp 127-129° C.

Analysis for $C_{18}H_{20}N_2O_8S$; Calc'd: C, 50.9; H, 4.8; N, 6.6. Found: C, 50.9; H, 4.8; N, 6.5. $^1$H NMR(300 MHz, CDCl$_3$): δ 2.06 (m, 1H), 3.51 (s, 3H), 3.89 (s, 3H), 3.92 (m, 2H), 4.59 (t, 1H, J=5.7 Hz); 4.83 (d, 1H, J=18 Hz); 4.96 (d, 1H, J=18 Hz), 6.96 (d, 2H, J=6.9 Hz), 7.43(m, 1H), 7.69(m, 1H), 7.76(d, 2H, J=6.8 Hz), 7.97(d, 1H, J=6), 8.03 (d, 1H, J=9 Hz); MS(ES):m/z 425.2(M+H)$^+$.

EXAMPLE 32

Methyl 2-[(2-aminobenzyl)-(4-methoxybenzenesulfonyl)amino]-3-hydroxypropionate

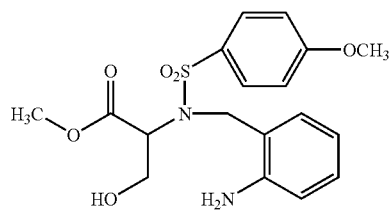

To a mixture, under nitrogen, of methyl 3-hydroxy-2-[(4-methoxybenzenesulfonyl)-(2-nitrobenzyl)amino]propionate (1.5 g, 3.53 mmol) in dry ethanol (5 ml) was added ammonium formate (1.12 g, 17.69 mmol) followed by the addition of 10% palladium on carbon (0.50 g). The mixture was stirred overnight at room temperature and then heated at 80° C. for 2 hours. The mixture was filtered through diatomaceous earth and the filtrate concentrated to dryness in vacuo to give a semisolid. Trituration with ethyl acetate gave 0.65 g (47%) of white crystals, m.p. 138-140° C.

Analalysis. for $C_{18}H_{22}N_2O_6S$; Calc'd: C, 54.8; H, 5.6; N, 7.1. Found: C, 53.0; H, 5.6; N, 6.8. $^1$H NMR(300 MHz, CDCl$_3$): δ 1.6 (broad, 1H), 3.29 (dd, 1H, J=6 Hz), 3.56 (s, 3H), 3.78 (m, 1H), 3.89 (s, 3H); 4.2 (d, 1H, J=15 Hz); 4.62 (d, 1H, J=15 Hz), 4.71 (m, 1h), 6.67 (d, 2H, J=6 Hz), 6.98 (d, 1H, J=6 Hz), 7.01 (m, 2H), 7.12 (m, 1H), 7.84 (m, 2h); MS(ES):m/z 395.3(M+H)$^+$.

EXAMPLE 33

Methyl 2-[(2-acetylaminobenzyl)-(4-methoxybenzenesulfonyl)-amino]acrylate

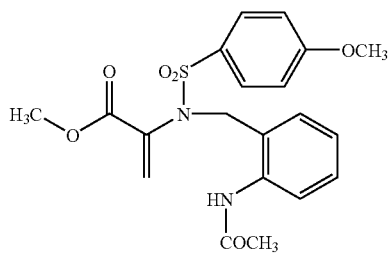

A mixture of methyl 2-[(2-aminobenzyl)-(4-methoxybenzenesulfonyl)amino]-3-hydroxypropionate (8.0 g, 20.28 mmol) in methylene chloride (60 ml) was cooled to 0° C. and triethylamine (12.69 ml, 91.1 mmol) in methylene chloride (25 ml)was added, followed by the addition of acetyl chloride (4.34 ml, 60.84 mmol). The mixture was stirred at room temperature overnight and diluted with methylene chloride. The mixture was washed with water, 2N citric acid, saturated sodium chloride and then dried with anhydrous sodium sulfate. The solvent was removed in vacuo to give 8.6 g of a yellow oil.

Analysis. for $C_{20}H_{22}N_2O_6S$; Calc'd: C, 57.40; H, 5.30; N, 6.69. Found: C, 55.34; H, 5.19; N, 6.02. $^1$H NMR(300 MHz, CDCl$_3$): δ 2.31 (s, 3H), 3.67 (s, 3H), 3.91 (s, 3H), 4.44 (s, 2h), 5.46(s, 1H); 6.27(s, 1H); 6.82(d, 1H, J=6.6 Hz), 7.02(m, 1H), 7.03(d, 2H, J=6Hz), 7.28 (m, 1H), 7.77 (d, 2H, J=6 Hz), 8.05 (d, 1H, J=8 Hz), 8.6 (br, 1H); MS(ES):m/z 418.9(M+H)$^+$.

EXAMPLE 34

2-[(2-Benzoylamino-benzyl)-(4-methoxy-benzenesulfonyl)-amino]-acrylic acid methyl ester

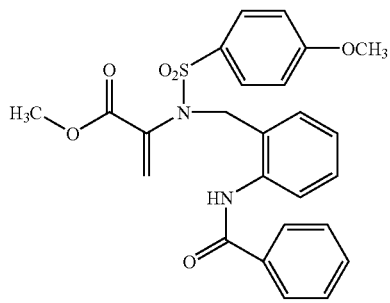

The procedure of Example 33 was followed using the product from Example 32 (500 mg, 1.268 mmol), triethylamine (0.884 ml, 6.34 mmol), and benzoyl chloride (0.324 ml, 2.79 mmol) in methylene chloride (60 ml) to give 620 mg (100%) of the product.

$^1$H NMR(300 MHz, CDCl$_3$): δ 3.5 (s, 3H), 3.89 (s, 3H), 4.48 (s, 2H), 5.37 (s, 1H); 6.25 (s, 1H); 6.8 (m, 1H), 6.99 (m, 3H), 7.38 (m, 1H), 7.56 (m, 3H), 7.72 (m, 2H), 8.18 (m, 3H), 9.29 (s, 1H). MS (ES):m/z 480.9 (M+H).

EXAMPLE 35

Methyl 1-acetyl-4-(4-methoxybenzenesulfonyl)-2,3,4,5-tetrahydro-1H-[1,4]benzodiazepine-3-carboxylate

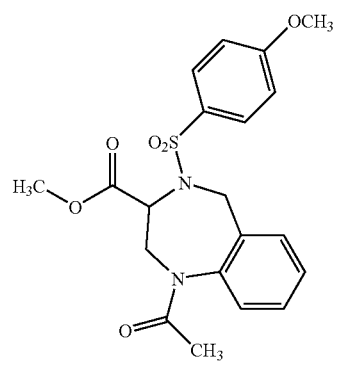

To a solution of methyl 2-[(2-acetylamino-benzyl)-(4-methoxybenzenesulfonyl)amino]acrylate (8.40 g, 20.07 mmol) in anhydrous methanol (5 ml) was added anhydrous sodium bicarbonate (2.19 g, 26.09 mmol) and the mixture was stirred at room temperature overnight. Anhydrous sodium bicarbonate (2.2 g) was added and the mixture was stirred for 18 hours, heated to 50° C. for three hours and the solvent removed in vacuo. The residue was dissolved in water and ethyl acetate. The organic layer was separated, washed with saturated sodium chloride and dried with anhydrous sodium sulfate. The solvent was removed in vacuo and the residue dried in vacuo to give 6.64 g of white crystals, m.p. 150-155° C.

Analysis for $C_{20}H_{22}N_2O_6S$: Calc'd: C, 57.40; H, 5.30; N, 6.69. Found: C, 57.47; H, 5.29; N, 6.62. $^1$H NMR(300 MHz, CDCl$_3$): δ 1.82 (s, 3H), 2.93 (dd, 1H, J=12 Hz), 3.68 (s, 3H), 3.84 (s, 3H), 4.61 (d, 2H, J=15 Hz); 4.93 (d, 1H, J=15 Hz); 5.12 (d, 1H, J=15 Hz), 6.98 (d, 2H J=9 Hz), 7.13 (dd, 1H, J=6 Hz), 7.33 (m, 2H), 7.48 (dd, 1H, J=6 Hz), 7.62 (d, 2H, J=9 Hz); MS(ES):m/z 419.1 (M+H)$^+$.

EXAMPLE 36

1-Benzoyl-4-(4-methoxy-benzenesulfonyl)-2,3,4,5-tetrahydro-1H-[1,4]benzodiazepine-3-carboxylic acid methyl ester

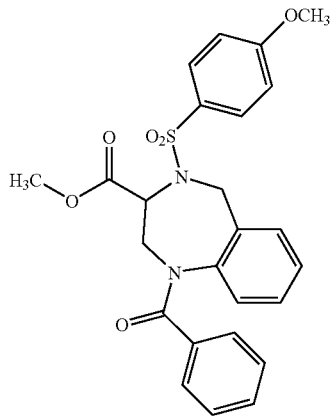

The procedure of Example 35 was followed using the product from Example 34 (500 mg, 1.04 mmol) and sodium bicarbonate (114 mg, 1.35 mmoml) in methanol (5 ml) to give 460 mg (92%) of the product.

$^1$H NMR(300 MHz, CDCl$_3$): δ 3.07 (b, 1H), 3.64 (s, 3H), 3.84 (s, 3H), 4.88 (d, 2H, J=14.55 Hz); 5.31 (b, 1H); 5.57 (b, 1H), 6.59(d, 1H, J=7.23 Hz), 6.93(m, 3H), 7.15 (m, 4H), 7.22 (m, 1H), 7.38 (m, 2H), 7.67 (m, 2H). MS (ES):m/z 480.9 (M+H).

EXAMPLE 37

Methyl 1-acetyl-4-(4-hydroxybenzenesulfonyl)-2,3,4,5-tetrahydro-1H-[1,4]-benzodiazepine-3-carboxylate

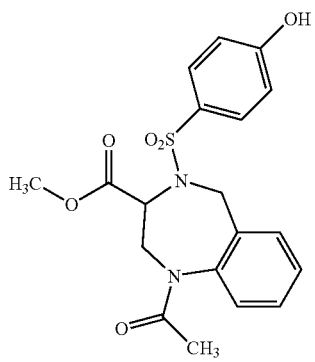

To a 0° C. solution of methyl 1-acetyl-4-(4-methoxybenzenesulfonyl)-2,3,4,5-tetrahydro-1H-[1,4]benzodiazepine-3-carboxylate (9.8 g, 23.42 mmol) in methylene chloride (50 ml) was added, dropwise, a 1.0 molar solution of boron tribromide (51.52 ml, 51.52 mmol) in methylene chloride and the mixture was stirred overnight at room temperature. Ice and water were added to the reaction mixture and the insolubles filtered off. The filtrate was diluted with methylene chloride and water. The organic layer was separated, washed with saturated sodium chloride and dried over anhydrous sodium sulfate. The solvent was removed in vacuo to give a crude product, which was purified by chromatography on silica gel (hexane:ethyl acetate (I:1)) to give 3.2 g of product as a white foam.

Anal. for $C_{19}H_{20}N_2O_6S$: Calc'd: C, 56.43; H, 4.98; N, 6.93. Found: C, 55.07; H, 4.72; N, 6.47. $^1$H NMR(300 MHz, CDCl$_3$): δ 1.69 (br, 1H), 1.89 (s, 3H), 2.95 (dd, 1H, J=12 Hz), 3.56 (s, 3H), 4.6 (br, 2H); 4.64 (d, 1H, J=115 Hz); 5.06 (d, 1H, J=12 Hz), 5.15 (d, 1H, J=12 Hz), 6.78 (d, 2H, J=9 Hz), 7.08 (t, 1H, J=6 Hz), 7.28 (t, 1H, J=6 Hz), 7.41 (d, 1H, J=6 Hz), 7.5 (d, 2H, J=9 Hz), 7.6 (d, 1H, J=6 Hz); MS(ES): m/z 404.9 (M+H)$^+$.

EXAMPLE 38

1-Benzoyl-4-(4-hydroxy-benzenesulfonyl)-2,3,4,5-tetrehydro-1H-benzo[e][1,4]diazepine-3-carboxylic acid methyl ester

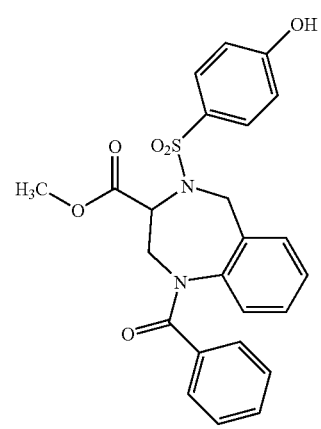

The procedure of Example 37 was followed using the product from Example 36 (9.8 g, 20.4 mmol), 1M solution of boron tribromide (40.8 ml, 40.8 mmol) in methylene chloride (50 ml) to give 4.8 grams (50%) of the product.

$^1$H NMR(300 MHz, CDCl$_3$): δ 3.05 (b, 1H), 3.63 (s, 3H), 4.87 (b, 2H), 5.28 (b, 1H), 5.55 (b, 1H); 6.6 (b, 2H), 6.82 (d, 2H, J=8.7 Hz), 6.98 (b, 1H), 7.15 (b, 4H), 7.23 (b, 1H), 7.40 (b, 1H), 7.63 (d, 2H, J=7.8). MS (ES):m/z 466.9 (M+H).

EXAMPLE 39

Methyl 1-acetyl-4-{[4-but-(2,3-butadienyloxy)phenyl]sulfonyl}-2,3,4,5-tetrahydro-1H-1,4-benzodiazepine-3-carboxylate

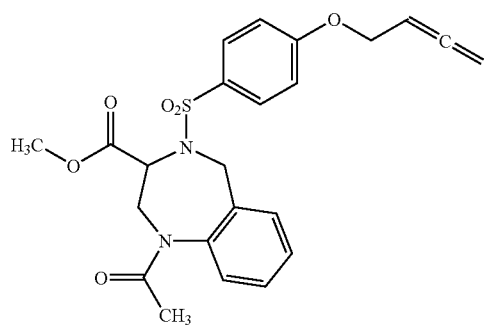

To a stirred solution of triphenylphosphine (525 mg, 2.0 mmol) in toluene (5 ml) was added buta-2,3-diene-1-ol (140 mg, 2.0 mmol) in tetrahydrofuran (5 ml) followed by methyl 1-acetyl-4-(4-hydroxybenzenesulfonyl)-2,3,4,5-tetrahydro- 1H-[1,4]benzodiaze-pine-3-carboxylate (750 mg, 1.85 mmol). To this solution, under nitrogen, was added slowly, dropwise, diethyl azodicarboxylate. (0.315 ml, 2.0 mmol). The mixture was stirred at room temperature overnight and concentrated to dryness in vacuo. The residue was purified by chromatography on silica gel preparative plates (ethyl acetate:hexane (1:1)) to give 670 mg of white crystals m.p. 80° C.-85° C.

IR(KBR): 3040, 1966, 1748, 1697, 1249, 1028 cm$^{-1}$; $^1$H NMR(300 MHz, CDCl$_3$): δ 1.86 (s, 3H), 2.96 (dd, 1H, J=4.2), 3.67(s, 3H), 4.6 (m, 2H); 4.66 (br, 1H), 4.69 (d, 1H, J=12 Hz), 4.89 (m, 2H), 5.07 (d, 1H, J=12 Hz), 5.15 (d, 1H, J=12 Hz), 5.35 (m, 1H), 6.9 (d, 2H, J=6 Hz), 7.13 (dd, 1H, J=4Hz), 7.33 (dd, 1H, J=4 Hz), 7.47 (d, 1H, J=3 Hz), 7.63 (d, 1H, J=3 Hz), 7.67 (m, 2H); MS(ES):m/z 457.2 (M+H)$^+$.

EXAMPLE 40

Methyl 1-benzoyl-4-{[4-(2,3-pentadienyloxy)phenyl]sulfonyl}-2,3,4,5-tetrahydro-1H-1,4-benzodiazepine-3-carboxylate

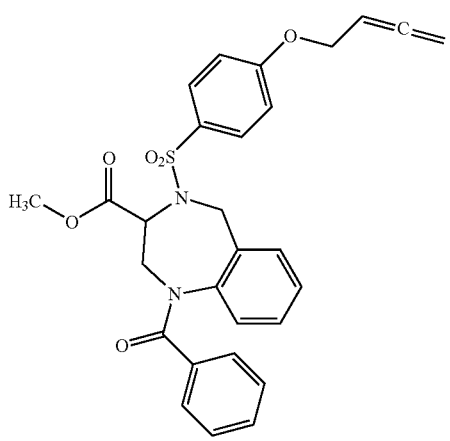

The procedure of Example 39 was followed using the product from Example 38 (650 mg, 1.39 mmol), buta-2-3diene-1-ol (1.05 mg, 1.5 mmol), triphenylphosphine (393 mg, 1.50 mmol), diethy azodicarboxylate (0.273 ml, 1.50 mmol), and tetrahydofuran (0.4 ml) in toluene (3 ml) to give 300 mg (42%) of the product.

IR(KBR): 2954, 1959, 1750, 1634, 1494, 1329, 1157, 839 cm$^{-1}$; $^1$H NMR(300 MHz, CDCl$_3$): δ 3.06 (b, 1H), 3.6 (s, 3H), 4.59 (m, 2H), 4.88 (m, 4H); 5.35 (m, 2H); 5.56 (b, 1H), 6.59 (d, 1H, J=5.6 Hz), 6.92 (m, 2H), 6.97 (b, 1H), 7.14 (m, 5H), 7.24 (b, 1H), 7.42 (b, 1H), 7.71 (b, 2H). MS (ES):m/z 518.9 (M+H).

EXAMPLE 41

Methyl 1-benzoyl-4-{[4-(2,3-pentadienyloxy)phenyl]sulfonyl}-2,3,4,5-tetrahydro-1H-1,4-benzodiazepine-3-carboxylate

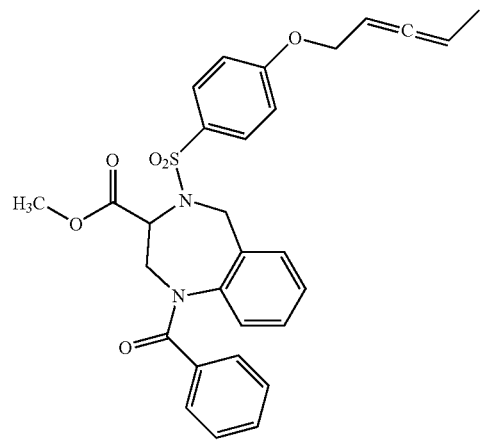

The procedure of Example 39 was followed using the product from Example 38 (840 mg, 1.80 mmol), penta-2,3-diene-1-ol (197 mg, 2.34 mmoml), triphenylphosphine (614 mg, 2.34 mmol), diethy azodicarboxylate (0.367 ml, 2.34 mmol) and tetrahydofuran (0.6 ml) in toluene (4 ml) to give 310 mg (32%) of the product.

IR(KBR): 2953, 1971, 1749, 1636, 1329, 1157, 767 cm$^{-1}$; $^1$H NMR(300 MHz, CDCl$_3$): δ 1.67 (m, 3H), 3.06 (b, 1H), 3.64 (s, 3H), 4.57(m, 2H); 4.87 (d, 2H, J=11.2); 5.28 (m, 3H), 5.55 (b, 1H), 6.58 (d, 2H, J=5.55), 6.95 (m, 4H), 7.14 (m, 5H), 7.43 (b, 1H), 7.69 (b, 2H). MS(ES):m/z 532.8 (M+H).

EXAMPLE 42

1-Acetyl-4-{[4-(2,3-butadienyloxy)phenyl]sulfonyl}-2,3,4,5-tetrahydro-1H-1,4-benzodiazepine-3-carboxylic acid

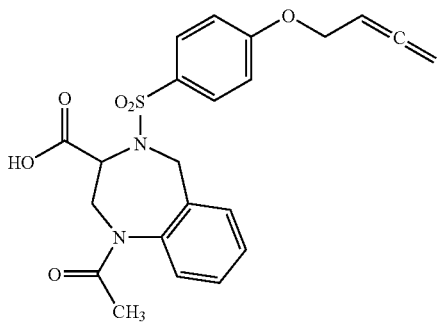

To a solution of methyl 1-acetyl-4-{[4-but(2,3butadienyloxy)phenyl]sulfonyl}-2,3,4,5-tetrahydro-1H-1,4-benzodiazepine-3-carboxylate (550 mg, 1.21 mmol) in tetrahydrofuran (1 ml), methanol (1 ml) and, water (5 ml) was added lithium hydroxide hydrate (127 mg, 3.03 mmol). The mixture was stirred at room temperature for 1 hour and concentrated in vacuo to dryness. Water was added to the residue and washed with diethyl ether, acidified with 2N hydrochloric acid, extracted with ethyl acetate, washed with saturated sodium chloride and dried over anhydrous sodium sulfate. The solvent was removed in vacuo and the residue dried in vacuo to give 525 mg of a white foam.

IR(KBR): 3245, 3040, 1957, 1746, 1624, 1252, 1154, 895 cm$^{-1}$; $^1$H NMR(300 MHz, CDCl$_3$): δ 1.88 (s, 3H), 3.0 (dd, 1H, J=4.2 Hz), 4.53 (m, 2H), 4.66 (m, 2H); 4.86 (m, 2H,); 5.13 (d, 1H, J=15 Hz), 5.37 (m, 2H), 6.52 (b, 1H), 6.84 (d, 2H, J=15 Hz), 7.12 (m, 1H), 7.35 (m, 1H), 7.46 (m, 1H), 7.55 (m, 1H), 7.65 (m, 2H). Analysis. for C$_{22}$H$_{22}$N$_2$O$_6$S. Calcl'd: C, 59.72, H, 5.01; N, 6.33. Found: C, 57.00; H, 5.43: N, 6.85. MS(ES):m/z 443.2 (M+H)$^+$.

EXAMPLE 43

1-Benzoyl-4-(4-buta-2,3-dienyloxy-benzenesulfonyl)-2,3,4,5-tetrahydro-1H-benzo[e][1,4]diazepine-3-carboxylic acid

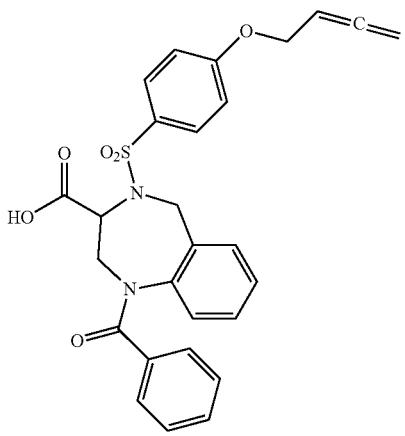

The procedure of Example 42 was followed using the product from Example 40 (270 mg, 0.521 mmol), lithium hydroxide (55 mg, 1.3 mmol) in water (0.4 ml), methanol (1 ml) and tetrahydrofuran (1 ml) to give 260 mg (99%) of the product.

IR(KBR): 3390, 2939, 1957, 1741, 1594, 1495, 1155, 1093, 833 cm$^{-1}$; $^1$H NMR(300 MHz, CDCl$_3$): δ 3.06 (b, 1H), 3.05-3.7 (b, 1H), 4.5 (m, 2H); 4.83 (b, 2H), 4.89 (m, 2H), 5.18 (b, 1H), 5.36 (m, 1H), 5.65 (b, 1H), 6.57(d, 1H, J=5.6 Hz) 6.89 (m, 2H), 6.98 (b, 1H); 7.13 (m, 5H), 7.28 (b, 1H), 7.43 (b, 1H), 7.67 (d, 2H, J=5.6 MS (ES):m/z 502.9 (M–H).

EXAMPLE 44

1-Benzoyl-4-{[4-(2,3-pentadienyloxy)phenyl]sulfonyl}-2,3,4,5-tetrahydro-1H-1,4-benzodiazepine-3-carboxylic acid

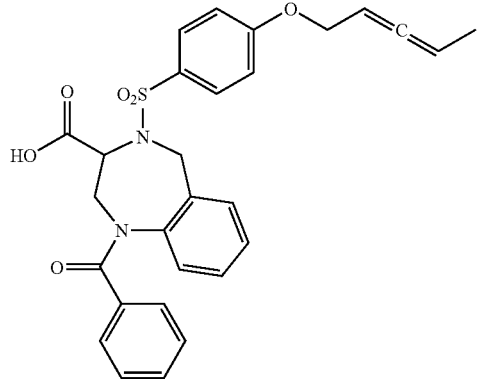

The procedure of Example 42 was followed using the product from Example 41 (280 mg, 0.526 mmol), lithium hydroxide (55 mg, 1.32 mmol) in water (0.4 ml), methanol (1 ml) and tetrahydrofuran (1 ml) to give 260 mg (95%) of the product.

IR(KBR): 3436, 2945, 1969, 1748, 1595, 1495, 1317, 1154, 808 cm$^{-1}$; $^1$H NMR(300 MHz, CDCl$_3$): δ 1.67 (m, 3H), 2.2-2.9 (b, 1H), 3.02 (b, 1H), 4.56 (m, 2H); 4.83 (b, 2H); 5.26 (m, 3H), 5.65 (b, 1H), 6.57 (d, 2H, J=5.7), 6.94 (m, 3H) 7.14 (m, 4H), 7.26 (m, 2H), 7.43 (b, 1H), 7.67 (d, 2H, J=5.7). MS (ES):m/z 516.9 (M–H).

EXAMPLE 45

1-Acetyl-4-{[4-(2,3-butadienyloxy)phenyl]sulfonyl}-N-hydroxy-2,3,4,5-tetrahydro-1H-1,4-benzodiazepine-3-carboxamide

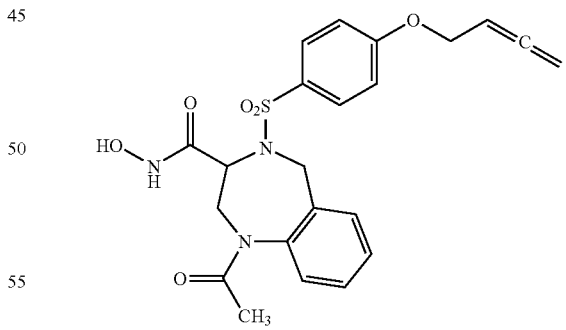

To a stirred solution of 1-acetyl-4-{[4-(2,3-butadienyloxy)phenyl]sulfonyl}-2,3,4,5-tetrahydro-1H-1,4-benzenediazepine-3-carboxylic acid(400 mg, 0.90 mmol) in methylenen chloride (3 ml) and dimethylformamide (1 ml) was added 1-hydroxybenzo-triazole (147 mg, 1.08 mmol) and 1-[3-(dimethylamino)propyl]-3-ethylcarbodiimide hydrochloride (225 mg, 1.18 mmol). The solution was stirred for 1 hour and hydroxylamine (477 μl, 7.23 mmol, 50% solution in H$_2$O) was added. The reaction was stirred at room temperature for 24 hours, diluted with methylene chloride, washed with water and concentrated in vacuo. The crude product was purified by chromatography on silica gel preparative plates (10% MeOH in EtOAc) to give 228 mg of a white foam.

IR(KBR): 3180, 2962, 1956, 1660, 1494, 1260, 1153, 1028, 802 cm$^{-1}$; $^1$H NMR(300 MHz, DMSO-d$_6$): δ 1.73 (s, 3H), 4.62 (m, 2H), 4.85 (br, 4H,) 4.99 (m, 2H); 5.18(br, 1H), 5.48(m, 1H), 6.99(d, 2H, J=8 Hz), 7.2 (br, 2H), 7.59 (m, 4H) 9.0 (br, 1H), 11.0 (br, 1H); Analysis for C$_{22}$H$_{23}$N$_3$O$_6$S Calc'd: C, 57.76; H, 5.07; N, 9.18. Found: C, 58.98; H, 5.55; N, 7.78. MS(ES):m/z 458.2 (M+H)+.

EXAMPLE 46

1-Benzoyl-4-(4-buta-2,3-dienyloxy-benzenesulfonyl)-2,3,4,5-tetrahydro-1H-benzo[e][1,4]diazepine-3-carboxylic acid hydroxyamide

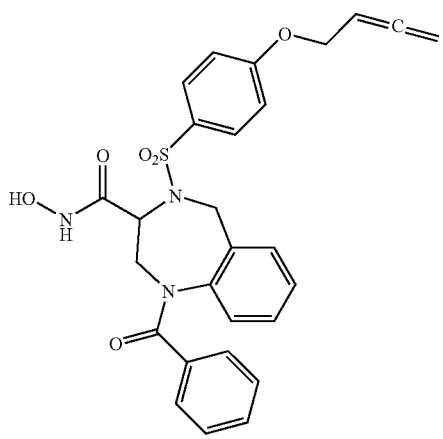

The procedure of Example 45 was followed using the product from Example 43 (230 mg, 0.456 mmol), 1-hydroxybenzotriazol (111 mg, 0.821 mmol), 1-[3-(dimethylamino) propyl]-3-ethylcarbodiimide hydrochloride (157 mg, 0.821 mmol), hydroxylamine in water 50% solution (0.251 ml, 4.1 mmol) in dimethylformamide (3 ml) to give 95 mg (40%) of the product.

IR(KBR): 3224, 2962, 1956, 1643, 1494, 1323, 1154, 766 cm$^1$; $^1$H NMR(300 MHz, DMSO-d$_6$): δ 3.32 (b, 1H), 4.64 (m, 2H), 4.78 (br, 2H,) 5.0 (m, 2H); 5.26 (br, 1H), 5.5 (m, 2H), 6.5 (b, 2H), 6.89 (br, 1H), 7.06 (m, 2H), 7.28 (m, 5H), 7.7 (b, 2H), 8.97 (br, 1H), 11.0 (br, 1H); MS (ES):m/z 519.8 (M+H).

EXAMPLE 47

1-Benzoyl-N-hydroxy-4-{[4-(2,3-pentadienyloxy)phenyl]sulfonyl}-2,3,4,5-tetrahydro-1H-1,4-benzodiazepine-3-carboxamide

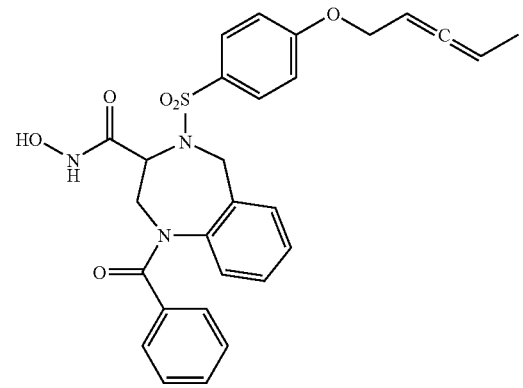

The procedure of Example 45 was followed using the product from Example 44 (230 mg, 0.444 mmol), 1-hydroxybenzotriazol (72 mg, 0.533 mmol), 1-[3-(dimethylamino) propyl]-3-ethylcarbodiimide hydrochloride (111 mg, 0.579 mmol), hydroxylamine in water 50% solution (0.217 ml, 3.55 mmol) in dimethylformamide (3 ml) to give 130 mg (55%) of the product.

IR(KBR): 3220, 2962, 1968, 1645, 1494, 1323, 1261, 1154, 801 cm$^{-1}$; $^1$H NMR(300 MHz, DMSO): δ 1.59 (m, 3H), 4.62 (m, 3H), 4.79 (b, 3H); 5.34(m, 3H), 6.5 (b, 1H), 7.06 (m, 4H), 7.22 (m, 6H), 7.71 (b, 2H), 8.96 (b, 1H), 11.0 (b, 1H) MS (ES):m/z 531.8 (M–H).

What is claimed:
1. A compound of Formula (I):

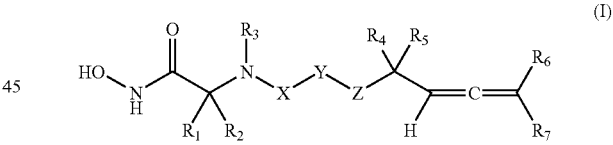

wherein:
X is —S—, —SO—, —SO$_2$— or —P(O)—R$_8$;
Y is aryl or heteroaryl, with the proviso that X and Z may not be bonded to adjacent atoms of Y;
Z is —O—, —NH—, —CH$_2$— or —S—;
R$_1$ is hydrogen, aryl, heteroaryl, C$_5$-C$_8$ cycloheteroalkyl, alkyl of 1 to 6 carbon atoms, alkenyl of 2 to 6 carbon atoms, or alkynyl of 2 to 6 carbon atoms;
R$_2$ is hydrogen, aryl, heteroaryl, cycloalkyl of 3 to 6 carbon atoms, C$_5$-C$_8$ cycloheteroalkyl, alkyl of 1 to 6 carbon atoms, alkenyl of 2 to 6 carbon atoms, or alkynyl of 2 to 6 carbon atoms;
or R$_1$ and R$_2$, taken together with the atoms to which they are attached, may form a 3 to 7 membered cycloalkyl or cycloheteroalkyl ring;
R$_3$ is hydrogen, cycloalkyl of 3 to 6 carbon atoms, alkyl of 1 to 6 carbon atoms, alkenyl of 2 to 6 carbon atoms, alkynyl of 2 to 6 carbon atoms;

or $R_1$ and $R_3$, together with the atoms to which they are attached, may form a 5 to 8 membered ring wherein $R_1$ and $R_3$ represent divalent moieties of the formulae:

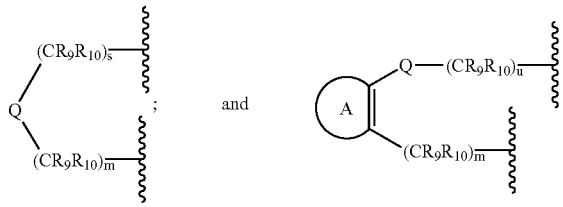

A is aryl or heteroaryl;
Q is a C—C single or double bond, —O—, —S—, —SO—, —SO$_2$—, —NR$_{11}$, or —CONR$_{12}$;
s is an integer of 0 to 3;
u is an integer of 1 to 4;
m is an integer of 1 to 3;
$R_4$ and $R_5$ are each, independently, hydrogen or alkyl of 1 to 6 carbon atoms;
$R_6$ and $R_7$ are each, independently, hydrogen, alkyl of 1 to 6 carbon atoms, cycloalkyl of 3 to 6 carbon atoms, aryl, heteroaryl or $C_5$-$C_8$-cycloheteroalkyl;
or $R_6$ and $R_7$, together with the atom to which they are attached, may form 3 to 7 membered cycloalkyl or cycloheteroalkyl ring;
$R_8$ is alkyl of 1 to 6 carbon atoms, cycloalkyl of 3 to 6 carbon atoms, aryl or heteroaryl;
$R_9$ and $R_{10}$ are each, independently, selected from H, —OR$_{13}$, —NR$_{13}$R$_{14}$, alkyl of 1 to 6 carbon atoms, alkenyl of 2 to 6 carbon atoms, alkynyl of 2 to 6 carbon atoms, cycloalkyl of 3 to 6 carbon atoms, aryl, heteroaryl, —COOR$_{13}$; or —CONR$_{13}$R$_{14}$; or $R_9$ and $R_{10}$ taken together form a $C_3$-$C_6$-cycloalkyl of 3 to 6 carbon atoms or a $C_5$-$C_8$-cycloheteroalkyl ring; or $R_9$ and $R_{10}$ taken together with the carbon to which they are attached, form a carbonyl group;
$R_{11}$ is hydrogen, alkyl of 1 to 6 carbon atoms, cycloalkyl of 3 to 6 carbon atoms, cycloheteroalkyl of 3 to 6 carbon atoms, aryl, heteroaryl, —S(O)$_n$R$_{13}$, —COOR$_{13}$, —CONR$_{13}$R$_{14}$, —SO$_2$NR$_{13}$R$_{14}$ or —COR$_{13}$, and n is an integer of 0 to 2;
$R_{12}$ is hydrogen, aryl, heteroaryl, alkyl of 1-6 carbon atoms or cycloalkyl of 3-6 carbon atoms; and
$R_{13}$ and $R_{14}$ are each, independently, hydrogen, alkyl of 1-6 carbon atoms, cycloalkyl of 3-6 carbon atoms, aryl, heteroaryl or $C_5$-$C_8$-cycloheteroalkyl;
or a pharmaceutically acceptable salt thereof.

2. A compound of claim 1 wherein Y is aryl and X is —SO$_2$— or a pharmaceutically acceptable salt thereof.

3. A compound of claim 2 wherein Y is phenyl or a pharmaceutically acceptable salt thereof.

4. A compound of claim 1 wherein Y is aryl and X is —SO$_2$—, Z is oxygen and $R_4$, $R_5$ and $R_6$ are hydrogen or a pharmaceutically acceptable salt thereof.

5. A compound of claim 4 wherein Y is phenyl or a pharmaceutically acceptable salt thereof.

6. A compound of claim 1 wherein Y is aryl and X is —SO$_2$— and Z is oxygen, $R_4$, $R_5$ and $R_6$ are hydrogen, $R_7$ is hydrogen or methyl and $R_2$ is isopropyl or a pharmaceutically acceptable salt thereof.

7. A compound of claim 6 wherein Y is phenyl or a pharmaceutically acceptable salt thereof.

8. A compound of claim 1 wherein Y is aryl and $R_1$ and $R_3$ together with the atoms to which each is attached form a thiomorpholine ring or a pharmaceutically acceptable salt thereof.

9. A compound of claim 8 wherein Y is phenyl or a pharmaceutically acceptable salt thereof.

10. A compound of claim 9 wherein the absolute stereochemistry is shown by the formula:

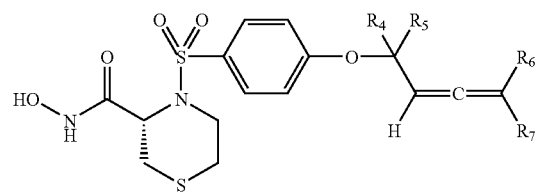

or a pharmaceutically acceptable salt thereof.

11. A compound of claim 1 selected from the group consisting of:
2-({[4-(2,3-Butadienyloxy)phenyl]sulfonyl}amino)-N-hydroxy-3-methylbutanamide,
2-[{[4-(2,3-Butadienyloxy)phenyl]sulfonyl}(methyl)amino]-N-hydroxy-3-methylbutanamide,
N-Hydroxy-3-methyl-2-({[4-(2,3-pentadienyloxy)phenyl]sulfonyl}amino)butanamide,
N-Hydroxy-3-methyl-2-(methyl{[4-(2,3-pentadienyloxy)phenyl]sulfonyl}amino)butanamide,
(3S)-4-{[4-(2,3- Butadienyloxy)phenyl]sulfonyl}-N-hydroxy-2,2-dimethyl-3-thiomorpholinecarboxamide,
(3S)-N-Hydroxy-2,2-dimethyl-4-{[4-(2,3-pentadienyloxy)phenyl]sulfonyl}-3-thiomorpholinecarboxamide,
1-Acetyl-4-{[4-(2,3-butadienyloxy)phenyl]sulfonyl}-N-hydroxy-2,3,4,5-tetrahydro-1H-1,4-benzodiazepine-3-carboxamide,
1-Benzoyl-4-(4-buta-2,3-dienyloxy-benzenesulfonyl)-2,3,4,5-tetrahydro-1H-benzo[e][1,4]diazepine-3-carboxylic acid hydroxyamide and
1-Benzoyl-N-hydroxy-4-{[4-(2,3-pentadienyloxy)phenyl]sulfonyl}-2,3,4,5-tetrahydro-1H-1,4-benzodiazepine-3-carboxamide.

12. A method of treating a pathological condition mediated by TNF-α converting enzyme (TACE) in a mammal in need thereof which comprises administering to said mammal a therapeutically effective amount of a compound having the formula

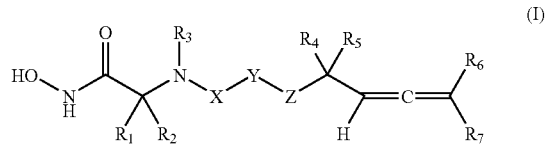

wherein:
X is —S—, —SO—, —SO$_2$— or —P(O)—R$_8$;
Y is aryl or heteroaryl, with the proviso that X and Z may not be bonded to adjacent atoms of Y;
Z is —O—, —NH—, —CH$_2$— or —S—;
$R_1$ is hydrogen, aryl, heteroaryl, $C_5$-$C_8$ cycloheteroalkyl, alkyl of 1 to 6 carbon atoms, alkenyl of 2 to 6 carbon atoms, alkynyl of 2 to 6 carbon atoms;

$R_2$ is hydrogen, aryl, heteroaryl, cycloalkyl of 3 to 6 carbon atoms, $C_5$-$C_8$ cycloheteroalkyl, alkyl of 1 to 6 carbon atoms, alkenyl of 2 to 6 carbon atoms, alkynyl of 2 to 6 carbon atoms;

$R_1$ and $R_2$, taken together with the atoms to which they are attached, may form a 3 to 7 membered cycloalkyl or cycloheteroalkyl ring;

$R_3$ is hydrogen, cycloalkyl of 3 to 6 carbon atoms, alkyl of 1 to 6 carbon atoms, or alkenyl of 2 to 6 carbon atoms;

or $R_1$ and $R_3$, together with the atoms to which they are attached, may form a 5 to 8 membered ring wherein $R_1$ and $R_3$ represent divalent moieties of the formulae:

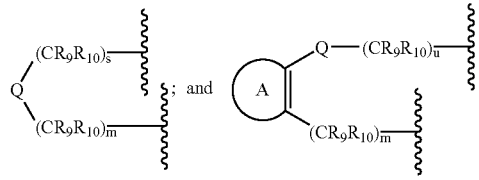

A is aryl or heteroaryl;
Q is a C—C single or double bond, —O—, —S—, —SO—, —SO$_2$—, —NR$_{11}$, or —CONR$_{12}$;
s is an integer of 0 to 3;
u is an integer of 1 to 4;
m is an integer of 1 to 3;
$R_4$ and $R_5$ are each, independently, hydrogen or alkyl of 1 to 6 carbon atoms;
$R_6$ and $R_7$ are each, independently, hydrogen, alkyl of 1 to 6 carbon atoms, aryl, heteroaryl or $C_5$-$C_8$-cycloheteroalkyl;
or $R_6$ and $R_7$, together with the atom to which they are attached, may form 3 to 7 membered cycloalkyl or cycloheteroalkyl ring;
$R_8$ is alkyl of 1 to 6 carbon atoms, cycloalkyl of 3 to 6 carbon atoms, aryl or heteroaryl;
$R_9$ and $R_{10}$ are each, independently, selected from H, —OR$_{13}$, —NR$_{13}$R$_{14}$, alkyl of 1 to 6 carbon atoms, alkenyl of 2 to 6 carbon atoms, alkynyl of 2 to 6 carbon atoms, cycloalkyl of 3 to 6 carbon atoms, aryl, heteroalryl, —COOR$_{13}$; or —CONR$_{13}$R$_{14}$; or $R_9$ and $R_{10}$ taken together form a $C_3$-$C_6$-cycloalkyl of 3 to 6 carbon atoms or a $C_5$-$C_8$-cycloheteroalkyl ring; or $R_9$ and $R_{10}$ taken together with the carbon to which they are attached, form a carbonyl group;
$R_{11}$ is hydrogen, alkyl of 1 to 6 carbon atoms, cycloalkyl of 3 to 6 carbon atoms, aryl, heteroalryl, —S(O)$_n$R$_{13}$, —COOR$_{13}$, —CONR$_{13}$R$_{14}$, —SO$_2$NR$_{13}$R$_{14}$ or —COR$_{13}$, and n is an integer of 0 to 2;
$R_{12}$ is hydrogen, aryl, heteroaryl, alkyl of 1-6 carbon atoms or cycloalkyl of 3-6 carbon atoms; and
$R_{13}$ and $R_{14}$ are each, independently, hydrogen, alkyl of 1-6 carbon atoms, cycloalkyl of 3-6 carbon atoms, aryl, heteroaryl or $C_5$-$C_8$-cycloheteroalkyl;
or a pharmaceutically acceptable salt thereof;
wherein the condition treated is rheumatoid arthritis, ulcerative colitis, multiple sclerosis, graft rejection, cachexia, inflammation, fever, insulin resistance, septic shock, congestive heart failure, inflammatory disease of the central nervous system, inflammatory bowel disease of HIV.

13. A pharmaceutical composition comprising a compound having the formula

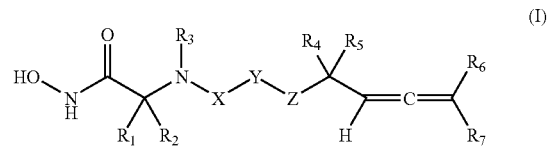

wherein:
X is —S—, —SO—, —SO$_2$— or —P(O)—R$_8$;
Y is aryl or heteroaryl, with the proviso that X and Z may not be bonded to adjacent atoms of Y;
Z is —O—, —NH—, —CH$_2$— or —S—;
$R_1$ is hydrogen, aryl, heteroaryl, $C_5$-$C_8$ cycloheteroalkyl, alkyl of 1 to 6 carbon atoms, alkenyl of 2 to 6 carbon atoms, alkynyl of 2 to 6 carbon atoms;
$R_2$ is hydrogen, aryl, heteroaryl, cycloalkyl of 3 to 6 carbon atoms, $C_5$-$C_8$ cycloheteroalkyl, alkyl of 1 to 6 carbon atoms, alkenyl of 2 to 6 carbon atoms, alkynyl of 2 to 6 carbon atoms;
or $R_1$ and $R_2$, taken together with the atoms to which they are attached, may form a 3 to 7 membered cycloalkyl or cycloheteroalkyl ring;
$R_3$ is hydrogen, cycloalkyl of 3 to 6 carbon atoms, alkyl of 1 to 6 carbon atoms, alkenyl of 2 to 6 carbon atoms, alkynyl of 2 to 6 carbon atoms;
or $R_1$ and $R_3$, together with the atoms to which they are attached, may form a 5 to 8 membered ring wherein $R_1$ and $R_3$ represent divalent moieties of the formulae:

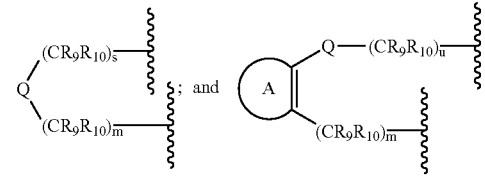

A is aryl or heteroaryl;
Q is a C—C single or double bond, —O—, —S—, —SO—, —SO$_2$—, —NR$_{11}$, or —CONR$_{12}$;
s is an integer of 0 to 3;
u is an integer of 1 to 4;
m is an integer of 1 to 3;
$R_4$ and $R_5$ are each, independently, hydrogen or alkyl of 1 to 6 carbon atoms;
$R_6$ and $R_7$ are each, independently, hydrogen, alkyl of 1 to 6 carbon atoms, aryl, heteroaryl or $C_5$-$C_8$-cycloheteroalkyl;
or $R_6$ and $R_7$, together with the atom to which they are attached, may form 3 to 7 membered cycloalkyl or cycloheteroalkyl ring;
$R_8$ is alkyl of 1 to 6 carbon atoms, cycloalkyl of 3 to 6 carbon atoms, aryl or heteroaryl;
$R_9$ and $R_{10}$ are each, independently, selected from H, —OR$_{13}$, —NR$_{13}$R$_{14}$, alkyl of 1 to 6 carbon atoms, alkenyl of 2 to 6 carbon atoms, alkynyl of 2 to 6 carbon atoms, aryl, heteroaryl, —COOR$_{13}$; or —CONR$_{13}$R$_{14}$; or $R_9$ and $R_{10}$ taken together form a $C_3$-$C_6$-cycloalkyl of 3 to 6 carbon atoms or a $C_5$-$C_8$-cycloheteroalkyl ring; or $R_9$ and $R_{10}$ taken together with the carbon to which they are attached, form a carbonyl group;
$R_{11}$ is hydrogen, alkyl of 1 to 6 carbon atoms, cycloalkyl of 3 to 6 carbon atoms, cycloheteroalkyl of 3 to 6 carbon atoms, aryl, heteroaryl, —S(O)$_n$R$_{13}$, —COOR$_{13}$, —CONR$_{13}$R$_{14}$, —SO$_2$NR$_{13}$R$_{14}$ or —COR$_{13}$, and n is an integer of 0 to 2;

R$_{12}$ is hydrogen, aryl, heteroaryl, alkyl of 1-6 carbon atoms or cycloalkyl of 3-6 carbon atoms; and R$_{13}$ and R$_{14}$ are each, independently, hydrogen, alkyl of 1-6 carbon atoms, cycloalkyl of 3-6 carbon atoms, aryl, heteroaryl or C$_5$-C$_8$-cycloheteroalkyl;

or a pharmaceutically acceptable salt thereof; and one or more pharmaceutically acceptable carriers.

14. A process for preparing a compound of Formula (I):

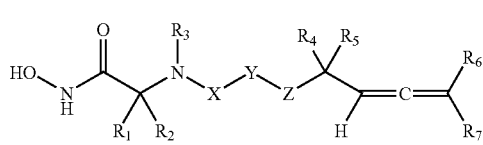

wherein:

Y is aryl or heteroaryl, with the proviso that X and Z may not be bonded to adjacent atoms of Y;

Z is —O—, —NH—, —CH$_2$— or —S—;

R$_1$ is hydrogen, aryl, heteroaryl, C$_5$-C$_8$ cycloheteroalkyl, alkyl of 1 to 6 carbon atoms, alkenyl of 2 to 6 carbon atoms, or alkynyl of 2 to 6 carbon atoms;

R$_2$ is hydrogen, aryl, heteroaryl, cycloalkyl of 3 to 6 carbon atoms, C$_5$-C$_8$ cycloheteroalkyl, alkyl of 1 to 6 carbon atoms, alkenyl of 2 to 6 carbon atoms, or alkynyl of 2 to 6 carbon atoms;

or R$_1$ and R$_2$, taken together with the atoms to which they are attached, may form a 3 to 7 membered cycloalkyl or cycloheteroalkyl ring;

R$_3$ is hydrogen, cycloalkyl of 3 to 6 carbon atoms, alkyl of 1 to 6 carbon atoms, alkenyl of 2 to 6 carbon atoms, or alkynyl of 2 to 6 carbon atoms;

or R$_1$ and R$_3$, together with the atoms to which they are attached, may form a 5 to 8 membered ring wherein R$_1$ and R$_3$ represent divalent moieties of the formulae:

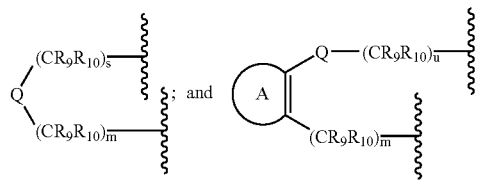

A is aryl or heteroaryl;

Q is a C—C single or double bond, —O—, —S—, —SO—, —SO$_2$—, —NR$_{11}$, or —CONR$_{12}$;

s is an integer of 0 to 3;

u is an integer of 1 to 4;

m is an integer of 1 to 3;

R$_4$ and R$_5$ are each, independently, hydrogen or alkyl of 1 to 6 carbon atoms;

R$_6$ and R$_7$ are each, independently, hydrogen, alkyl of 1 to 6 carbon atoms, aryl, heteroaryl or C$_5$-C$_8$-cycloheteroalkyl;

or R$_6$ and R$_7$, together with the atom to which they are attached, may form 3 to 7 membered cycloalkyl or cycloheteroalkyl ring;

R$_8$ is alkyl of 1 to 6 carbon atoms, cycloalkyl of 3 to 6 carbon atoms, aryl or heteroaryl;

R$_9$ and R$_{10}$ are each, independently, selected from H, —OR$_{13}$, —NR$_{13}$R$_{14}$, alkyl of 1 to 6 carbon atoms, alkenyl of 2 to 6 carbon atoms, alkynyl of 2 to 6 carbon atoms, aryl, heteroaryl, —COOR$_{13}$; or —CONR$_{13}$R$_{14}$; or R$_9$ and R$_{10}$ taken together form a C$_3$-C$_6$-cycloalkyl of 3 to 6 carbon atoms or a C$_5$-C$_8$-cycloheteroalkyl ring; or R$_9$ and R$_{10}$ taken together with the carbon to which they are attached, form a carbonyl group;

R$_{11}$ is hydrogen, alkyl of 1 to 6 carbon atoms, cycloalkyl of 3 to 6 carbon atoms, cycloheteroalkyl of 3 to 6 carbon atoms, aryl, heteroaryl, —S(O)$_n$R$_{13}$, —COOR$_{13}$, —CONR$_{13}$R$_{14}$, —SO$_2$NR$_{13}$R$_{14}$ or —COR$_{13}$, and n is an integer of 0 to 2;

R$_{12}$ is hydrogen, aryl, heteroaryl, alkyl of 1 to 6 carbon atoms or cycloalkyl of 3 to 6 carbon atoms; and R$_{13}$ and R$_{14}$ are each, independently, hydrogen, alkyl of 1 to 6 carbon atoms, cycloalkyl of 3 to 6 carbon atoms, aryl, heteroaryl or C$_5$-C$_8$-cycloheteroalkyl;

or a pharmaceutically acceptable salt thereof which comprises:

reacting a compound of the formula V:

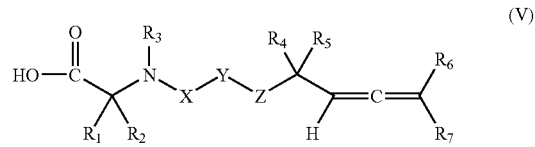

wherein R$_1$, R$_2$, R$_3$, R$_4$, R$_5$, R$_6$, R$_7$, X, Y and Z are as hereinbefore defined with an activating reagent forming an activating agent which is further reacted with hydroxylamine to give a corresponding compound of formula (I).

15. The process of claim 14 wherein the activating reagent is a chlorinating agent selected from the group consisting of thionyl chloride, chlorosulfonic acid, oxalyl chloride, and phosphorous pentachloride, or a halogenating agent selected from the group consisting of fluorosulfonic acid and thionyl bromide, a peptide coupling reagent selected from the group consisting of N,N'-Dicyclohexylcarbodiimide plus 1-hydroxybenzotriazole; Benzotriazol-1-yloxytris (dimethylamino)phosphonium hexafluorophosphate (BOP-reagent); N,N'-Bis[2-oxo-3-oxazolidinyl]phosphorodiamidic chloride (BOB-Cl); Diphenylphosphinyl chloride (DPP-Cl); Diethoxyphosphoryl cyanide; 2-Chloro-1-methylpyridinium iodide; Phenyldichlorophosphate plus imidazole; and ethyl chloroformate.

* * * * *